(12) United States Patent
Wang et al.

(10) Patent No.: US 10,370,338 B2
(45) Date of Patent: Aug. 6, 2019

(54) BENZAZEPINE DICARBOXAMIDE COMPOUNDS WITH TERTIARY AMIDE FUNCTION

(71) Applicant: Hoffmann-La Roche Inc., Little Falls, NJ (US)

(72) Inventors: Lisha Wang, Shanghai (CN); Hongying Yun, Shanghai (CN); Weixing Zhang, Shanghai (CN); Wei Zhu, Shanghai (CN); Zhiwei Zhang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/189,646

(22) Filed: Nov. 13, 2018

(65) Prior Publication Data

US 2019/0077763 A1    Mar. 14, 2019

Related U.S. Application Data

(63) Continuation of application No. PCT/EP2017/062059, filed on May 19, 2017.

(30) Foreign Application Priority Data

May 23, 2016    (WO) ................ PCT/CN2016/082993

(51) Int. Cl.
| | | |
|---|---|---|
| C07D 401/12 | (2006.01) |
| C07D 223/16 | (2006.01) |
| C07D 401/06 | (2006.01) |
| C07D 403/06 | (2006.01) |
| C07D 471/10 | (2006.01) |
| C07D 487/04 | (2006.01) |
| C07D 487/08 | (2006.01) |
| C07D 487/10 | (2006.01) |
| C07D 471/04 | (2006.01) |
| C07D 471/08 | (2006.01) |
| A61P 37/06 | (2006.01) |
| A61P 37/08 | (2006.01) |
| A61P 31/04 | (2006.01) |
| A61P 35/00 | (2006.01) |

(52) U.S. Cl.
CPC ......... *C07D 223/16* (2013.01); *C07D 401/06* (2013.01); *C07D 403/06* (2013.01); *C07D 471/04* (2013.01); *C07D 471/08* (2013.01); *C07D 471/10* (2013.01); *C07D 487/04* (2013.01); *C07D 487/08* (2013.01); *C07D 487/10* (2013.01); *A61P 31/04* (2018.01); *A61P 35/00* (2018.01); *A61P 37/06* (2018.01); *A61P 37/08* (2018.01)

(58) Field of Classification Search
CPC .. C07D 223/16; C07D 401/12; C07D 405/12; C07D 413/12; C07D 417/12; C07D 401/06; C07D 403/06; C07D 471/04; C07D 471/08; C07D 471/10; C07D 487/10

See application file for complete search history.

(56) References Cited

U.S. PATENT DOCUMENTS

| | | | |
|---|---|---|---|
| 9,334,268 B2 | 5/2016 | Hoves et al. | |
| 9,447,097 B2 | 9/2016 | Hoves et al. | |
| 9,475,775 B2* | 10/2016 | Hoves | C07D 223/16 |
| 9,597,333 B2* | 3/2017 | Hoves | C07D 223/16 |
| 9,822,065 B1* | 11/2017 | Hoves | C07D 223/16 |
| 9,890,124 B2* | 2/2018 | Hoves | C07D 403/12 |
| 2003/0187016 A1 | 10/2003 | Crooks et al. | |
| 2012/0082658 A1 | 4/2012 | Hershberg et al. | |
| 2013/0202629 A1 | 8/2013 | Carson et al. | |
| 2016/0257653 A1* | 9/2016 | Hoves | C07D 223/16 |
| 2017/0014423 A1* | 1/2017 | Hoves | C07D 223/16 |

(Continued)

FOREIGN PATENT DOCUMENTS

| | | |
|---|---|---|
| CA | 3023154 | 11/2017 |
| EP | 0825186 B1 | 4/2002 |

(Continued)

OTHER PUBLICATIONS

E. Smits, 13 The Oncologist, 859-875 (2008) (Year: 2008).*

(Continued)

*Primary Examiner* — Alexander R Pagano
(74) *Attorney, Agent, or Firm* — Todd M. Crissey

(57) ABSTRACT

This invention relates to new benzazepine dicarboxamide compounds of the formula

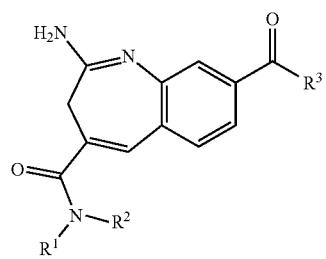

wherein $R^1$ to $R^3$ are as defined in the description and in the claims, as well as pharmaceutically acceptable salts thereof. These compounds are TLR agonists and may therefore be useful as medicaments for the treatment of diseases such as cancer, autoimmune diseases, inflammation, sepsis, allergy, asthma, graft rejection, graft-versus-host disease, immunodeficiencies, and infectious diseases.

21 Claims, No Drawings

(56) References Cited

U.S. PATENT DOCUMENTS

| | | | |
|---|---|---|---|
| 2017/0275253 A1* | 9/2017 | Hoves | C07D 403/12 |
| 2018/0134705 A1* | 5/2018 | Cheng | C07D 471/04 |
| 2018/0194735 A1* | 7/2018 | Hoves | C07D 401/04 |
| 2018/0194736 A1 | 7/2018 | Hoves et al. | |

FOREIGN PATENT DOCUMENTS

| | | |
|---|---|---|
| WO | 1992/015582 A1 | 9/1992 |
| WO | 2005/076783 A2 | 8/2005 |
| WO | 2007/024612 A2 | 3/2007 |
| WO | 2009/111337 A1 | 9/2009 |
| WO | 2010/054215 A1 | 5/2010 |
| WO | 2010/093436 A2 | 8/2010 |
| WO | 2011/017611 A1 | 2/2011 |
| WO | 2011/022508 A2 | 2/2011 |
| WO | 2011/022509 A2 | 2/2011 |
| WO | 2011/068233 A1 | 6/2011 |
| WO | 2011/139348 A2 | 11/2011 |
| WO | 2012/045090 A2 | 4/2012 |
| WO | 2012/066336 A1 | 5/2012 |
| WO | 2012/097173 A2 | 7/2012 |
| WO | 2012/167081 A1 | 12/2012 |
| WO | 2013/033345 A1 | 3/2013 |
| WO | 2013/067597 A1 | 5/2013 |
| WO | 2013/166110 A1 | 11/2013 |
| WO | 2015/162075 | 10/2015 |
| WO | 2016/096778 | 6/2016 |
| WO | 2016/096778 A1 | 6/2016 |
| WO | 2016/142250 A1 | 9/2016 |
| WO | 2017/046112 | 3/2017 |
| WO | 2017/190669 | 11/2017 |
| WO | 2017/202703 | 11/2017 |
| WO | 2017/202704 | 11/2017 |
| WO | 2017/216054 | 12/2017 |

OTHER PUBLICATIONS

C. Guiducci et al. 210 Journal of Experimental Medicine, 2903-2919 (2013) (Year: 2013).*

M. Zimmermann et al., Scientific Reports (Nature) (2016) (Year: 2016).*

(ISR and WO for PCT/EP2017/062058 dated Jun. 22, 2017).

(ISR and WO for PCT/EP2017/062059 dated Jun. 22, 2017).

(ISR and WO for PCT/EP2017/064107 dated Jul. 21, 2017).

Hennessy et al., "Targeting Toll-Like Receptors: Emerging Therapeutics?" Nature Reviews: Drug Discovery 9:293-307 (Apr. 2010).

Holldack, "Toll-Like Receptors as Therapeutic Targets for Cancer" Drug Discovery Today 19(4):379-382 (Apr. 2014).

International Search Report for PCT/EP2015/058465, dated May 26, 2015.

ISR and Written Opinion for PCT/EP2015/079679 (dated: Mar. 8, 2016).

ISR for PCT/EP2016/054487.

ISR for PCT/EP2016/071613 (Date of mailing Oct. 31, 2016).

Kawai et al., "The Role of Pattern-Recognition Receptors in Innate Immunity: Update on Toll-Like Receptors" Nature Immunology 11(5):373-384 (May 2010).

Kawai et al., "Toll-Like Receptors and Their Crosstalk with Other Innate Receptors in Infection and Immunity" Immunity 34:637-650 (May 27, 2011).

Uematsu et al., "Toll-Like Receptors and Type I Interferons" Journal of Biological Chemistry 282(21):15319-15323 (May 25, 2007).

Written Opinion for PCT/EP2015/058465.

Written Opinion for PCT/EP2016054487.

* cited by examiner

BENZAZEPINE DICARBOXAMIDE COMPOUNDS WITH TERTIARY AMIDE FUNCTION

RELATED APPLICATIONS

This application is a continuation of International Application No. PCT/EP2017/062059, filed May 19, 2017, claiming priority to Application No. PCT/CN2016/082993 filed May 23, 2016, each of which are incorporated herein by reference in its entirety.

FIELD OF THE INVENTION

The present invention relates to novel benzazepinedicarboxamide compounds having pharmaceutical activity, their manufacture, pharmaceutical compositions containing them and their potential use as medicaments.

In particular, the present invention relates to compounds of the formula

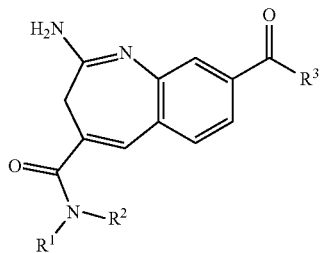

I wherein $R^1$ to $R^3$ are as described below, or to pharmaceutically acceptable salts thereof.

The compounds are TLR agonists. More particularly, the compounds are TLR8 agonists and may be useful for the treatment and prevention (e.g. vaccination) of cancer, autoimmune diseases, inflammation, sepsis, allergy, asthma, graft rejection, graft-versus-host disease, immunodeficiencies, and infectious diseases.

Toll-like receptors (TLRs) are a family of membrane-spanning receptors that are expressed on cells of the immune system like dendritic cells, macrophages, monocytes, T cells, B cells, NK cells and mast cells but also on a variety of non-immune cells such as endothelial cells, epithelial cells and even tumor cells (Kawai et al., Immunity, 2011, 34, 637-650, Kawai et al., Nat. Immunol., 2010, 11, 373-384). TLRs that recognize bacterial and fungal components are expressed on the cell surface (i.e. TLR1, 2, 4, 5 and 6), while others that recognize viral or microbial nucleic acids like TLR3, 7, 8 and 9 are localized to the endolysosomal/phagosomal compartment (Henessy et al. Nat. Rev. Drug Discovery 2010, 9, 293-307) and predominantly found to be expressed by cells of the myeloid lineage. TLR ligation leads to activation of NF-κB and IRF-dependent pathways with the specific activation sequence and response with respect to the specific TLR and cell type. While TLR7 is mainly expressed in all dendritic cells subtypes (DC and here highly in pDC, plasmacytoid DC) and can be induced in B cells upon IFNα stimulation (Bekeredjian-Ding et al. J. Immunology 2005, 174:4043-4050), TLR8 expression is rather restricted to monocytes, macrophages and myeloid DC. TLR8 signaling via MyD88 can be activated by bacterial single stranded RNA, small molecule agonists and lately discovered microRNAs (Chen et al. RNA 2013, 19:737-739). The activation of TLR8 results in the production of various pro-inflammatory cytokines such as IL-6, IL-12 and TNF-α as well as enhanced expression of co-stimulatory molecules, such as CD80, CD86, and chemokine receptors (Cros et al. Immunity 2010, 33:375-386). In addition, TLR8 activation can induce type I interferon (IFNβ) in primary human monocytes (Pang et al. BMC Immunology 2011, 12:55).

Small molecule agonists for both the TLR7 and TLR8 receptor as well as analogs modified for use as vaccine adjuvants or conjugates have been identified in many patents (i.e. WO1992015582, WO2007024612, WO2009111337, WO2010093436, WO2011017611, WO2011068233, WO2011139348, WO2012066336, WO2012167081, WO2013033345, WO2013166110, and US2013202629). Clinical experience has been obtained mainly for TLR7 agonists, but only very few clinical studies focused on using highly specific TLR8 agonists. To date, the only FDA (U.S. Food and Drug Administration)-approved small molecule drug is the TLR7 agonist imiquimod (ALDARA™) as a topical agent for the treatment of genital warts, superficial basal cell carcinoma and actinic keratosis. Systemic application however of the early TLR7 agonists like resiquimod has been abandoned due to intolerable cardiotoxicity observed upon global chemokine stimulation at therapeutic levels (Holldack, Drug Discovery Today, 2013, 1-4). Knowledge about TLR8 agonists is less advanced and mostly restricted to data with early mixed TLR7/8 agonists like resiquimod. For the resiquimod agonist, however, the stimulatory capacity of the TLR7 is superior compared to the activation of the TLR8, so that most of the effects of resiquimod are dominated by the effect of TLR7 activity. More recently, TLR8 specific compounds like VTX-2337 have been described by VentiRX Pharmaceuticals (i.e. WO 2007024612), allowing for the first time to analyse the specific role of TLR8 without activation of TLR7 at the same time. At present there is still a need for small molecule TLR8 agonists, specifically those with improved potency or selectivity.

The present invention is directed to benzazepine dicarboxamides with improved cellular potency over known TLR8 agonists of this type for use in the treatment of cancer, preferably solid tumors and lymphomas, and for other uses including the treatment of certain skin conditions or diseases, such as atopic dermatitis, the treatment of infectious diseases, preferably viral diseases, and for use as adjuvants in vaccines formulated for use in cancer therapy or by desensitizing of the receptors by continuous stimulation in the treatment of autoimmune diseases.

These new compounds are characterized by an improved cellular potency at TLR8 compared to known TLR8 agonists such as VTX-2337. In addition these compounds are highly specific towards TLR8 and possess only low or even no activity towards TLR7. Thus, they are expected to possess advantageous properties compared to combined TLR7/8 agonists due to the more restricted expression pattern of TLR8 resulting in less severe side effects when administered systemically.

SUMMARY OF THE INVENTION

The present invention relates to benzazepine dicarboxamide compounds of the formula

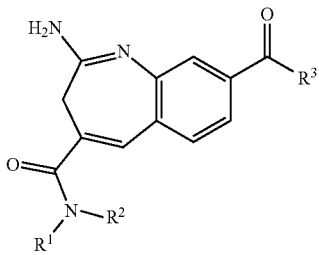

I wherein
R$^1$ is C$_{3-7}$-alkyl;
R$^2$ is C$_{3-7}$-alkyl or C$_{3-7}$-cycloalkyl-C$_{1-7}$-alkyl;
R$^3$ is a heterocycle selected from

a)

wherein
X$_1$ is (CH$_2$)$_m$ wherein m is 1 or 2;
X$_2$ is (CH$_2$)$_n$ wherein n is 1 or 2;
X$_3$ is (CH$_2$)$_o$ wherein o is 1 or 2;
X$_4$ is (CH$_2$)$_p$ wherein p is 1 or 2; and
Z$_1$ is phenyl, wherein phenyl is unsubstituted or substituted by one or two groups selected from the group consisting of C$_{1-7}$-alkyl, halogen, halogen-C$_{1-7}$-alkyl, C$_{1-7}$-alkoxy, hydroxy-C$_{1-7}$-alkyl, amino-C$_{1-7}$-alkyl, C$_{1-7}$-alkyl-amino-C$_{1-7}$-alkyl and di-C$_{1-7}$-alkyl-amino-C$_{1-7}$-alkyl; or

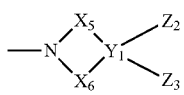

b)

wherein
X$_5$ is (CH$_2$)$_q$ wherein q is 1 or 2;
X$_6$ is (CH$_2$)$_r$ wherein r is 1 or 2;
Y$_1$ is a carbon or nitrogen atom and
Z$_2$ is hydrogen and
Z$_3$ is selected from the group consisting of hydrogen, C$_{1-7}$-alkoxy, C$_{2-7}$-alkenyloxy, phenyl, phenyl-C$_{1-7}$-alkyl, phenyl-C$_{1-7}$-alkyloxy, phenyl-C$_{1-7}$-alkyl amino, phenylamino-C$_{1-7}$-alkyl, phenylamino, wherein phenyl is unsubstituted or substituted by one or two groups selected from the group consisting of C$_{1-7}$-alkyl, halogen, halogen-C$_{1-7}$-alkyl, C$_{1-7}$-alkoxy, hydroxy-C$_{1-7}$-alkyl, amino-C$_{1-7}$-alkyl, C$_{1-7}$-alkyl-amino-C$_{1-7}$-alkyl and di-C$_{1-7}$-alkyl-amino-C$_{1-7}$-alkyl;

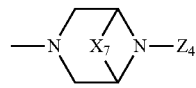

c)

wherein
X$_7$ is (CH$_2$)$_s$ wherein s is 1 or 2; and
Z$_4$ is phenyl, wherein phenyl is unsubstituted or substituted by one or two groups selected from the group consisting of C$_{1-7}$-alkyl, halogen, halogen-C$_{1-7}$-alkyl, C$_{1-7}$-alkoxy, hydroxy-C$_{1-7}$-alkyl, amino-C$_{1-7}$-alkyl, C$_{1-7}$-alkyl-amino-C$_{1-7}$-alkyl and di-C$_{1-7}$-alkyl-amino-C$_{1-7}$-alkyl; or

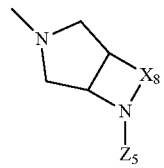

d)

wherein
X$_8$ is (CH$_2$)$_t$ wherein t is 1 or 2; and
Z$_5$ is phenyl, wherein phenyl is unsubstituted or substituted by one or two groups selected from the group consisting of C$_{1-7}$-alkyl, halogen, halogen-C$_{1-7}$-alkyl, C$_{1-7}$-alkoxy, hydroxy-C$_{1-7}$-alkyl, amino-C$_{1-7}$-alkyl, C$_{1-7}$-alkyl-amino-C$_{1-7}$-alkyl and di-C$_{1-7}$-alkyl-amino-C$_{1-7}$-alkyl,
or pharmaceutically acceptable salts thereof.

The invention is also concerned with processes for the manufacture of compounds of formula I.

The invention also relates to pharmaceutical compositions comprising a compound of formula I as described above and a pharmaceutically acceptable carrier and/or adjuvant.

A further aspect of the invention is the use of compounds of formula I as therapeutic active substances for the treatment of diseases that can be mediated with TLR agonists, in particular TLR8 agonists. The invention thus relates to a method for the treatment of a disease that can be mediated with TLR agonists such as for example cancer and autoimmune or infectious diseases.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

The nomenclature used in this application is based on IUPAC systematic nomenclature, unless indicated otherwise.

The term "compound(s) of this invention" and "compound(s) of the present invention" refers to compounds of formula I and solvates or salts thereof (e.g., pharmaceutically acceptable salts).

The term "substituent" denotes an atom or a group of atoms replacing a hydrogen atom on the parent molecule.

The term "lower alkyl" or "C$_{1-7}$-alkyl", alone or in combination with other groups, signifies a straight-chain or branched-chain optionally substituted alkyl group with 1 to 7 carbon atoms, in particular a straight or branched-chain alkyl group with 1 to 6 carbon atoms and more particularly a straight or branched-chain alkyl group with 1 to 4 carbon atoms. Examples of straight-chain and branched $C_{1-7}$-alkyl groups are methyl, ethyl, n-propyl, isopropyl, n-butyl, isobutyl, tert-butyl and pentyl or hexyl with its isomers. The term "$C_{3-7}$-alkyl" refers to a straight-chain or branched-chain alkyl group with 3 to 7 carbon atoms as defined above, however the methyl or ethyl group is excluded.

The term "$C_{2-7}$-alkenyl", alone or in combination, signifies a straight-chain or branched-chain hydrocarbon residue comprising an olefinic bond and 2 to 7, preferably 3 to 6, particularly preferred 3 to 4 carbon atoms. Examples of straight-chain and branched $C_{2-7}$-alkenyl groups are vinyl, propenyl and its isomers and butenyl and its isomers.

The term "$C_{1-7}$-alkoxy" refers to the group R'—O—, wherein R' is lower alkyl and the term "lower alkyl" has the previously given significance. Examples of $C_{1-7}$-alkoxy groups are methoxy, ethoxy, n-propoxy, isopropoxy, n-butoxy, isobutoxy, sec.-butoxy and tert-butoxy, in particular methoxy.

The term "$C_{2-7}$-alkenyloxy", alone or in combination, signifies a "$C_{2-7}$-alkenyl" group as defined above attached to an oxygen atom —O—, more particularly vinyloxy, propenoxy or butenoxy and its isomers.

The term "halogen" refers to fluoro, chloro, bromo and iodo, with fluoro, chloro and bromo being of particular interest. More particularly, halogen refers to fluoro.

The term "lower halogenalkyl" or "halogen-$C_{1-7}$-alkyl" refers to lower alkyl groups as defined above wherein at least one of the hydrogen atoms of the lower alkyl group is replaced by a halogen atom, particularly fluoro or chloro, most particularly fluoro. Among the lower halogenalkyl groups of particular interest are trifluoromethyl, difluoromethyl, trifluoroethyl, 2,2-difluoroethyl, fluoromethyl and chloromethyl, with trifluoromethyl being of more particular interest.

"Amino" refers to the group —$NH_2$. The term "$C_{1-7}$-alkylamino" means a group —NHR, wherein R is lower alkyl and the term "lower alkyl" has the previously given significance. The term "di-$C_{1-7}$-alkylamino" means a group —NRR', wherein R and R' are lower alkyl groups as defined above.

The term "lower aminoalkyl" or "amino-$C_{1-7}$-alkyl" refers to lower alkyl groups as defined above wherein at least one of the hydrogen atoms of the lower alkyl group is replaced by an amino group. Among the particular interesting lower aminoalkyl groups are aminomethyl or 2-aminoethyl.

The term "$C_{1-7}$-alkylamino", alone or in combination, signifies a "$C_{1-7}$-alkyl" group as defined above attached to an amino group, more particularly methylamino, ethylamino, propylamino and butylamino and its isomers. Methylamino is particularly preferred.

The term "phenylamino", alone or in combination, signifies a phenyl moiety attached to an amino group.

The term "amino-$C_{1-4}$-alkyl", alone or in combination, signifies an amino group attached to a "$C_{1-4}$-alkyl" group as defined above, more particularly to aminomethyl, aminoethyl or aminopropyl and aminobutyl and its isomers. Aminomethyl is particularly preferred.

The term "lower phenylalkyl" or "phenyl-$C_{1-7}$-alkyl" refers to lower alkyl groups as defined above wherein at least one of the hydrogen atoms of the lower alkyl group is replaced by a phenyl ring. Lower phenylalkyl groups of particular interest are phenylmethyl and 2-phenylethyl, with 2-phenylethyl being of particular interest.

The term "lower alkylphenyl" or "$C_{1-7}$-alkylphenyl" refers to a phenyl group that is substituted with at least one lower alkyl group as defined herein before. A lower alkylphenyl group of particular interest is methylphenyl, but also a dimethylphenyl group is included in the definition.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

Compounds of formula I can form pharmaceutically acceptable salts. The term "pharmaceutically acceptable salts" refers to those salts which retain the biological effectiveness and properties of the free bases or free acids, which are not biologically or otherwise undesirable. Pharmaceutically acceptable salts include both acid and base addition salts. The salts are for example acid addition salts of compounds of formula I with physiologically compatible mineral acids, such as hydrochloric acid, hydrobromic acid, nitric acid, carbonic acid, sulfuric acid, sulfurous acid or phosphoric acid; or with organic acids, such as methanesulfonic acid, ethanesulfonic acid, p-toluenesulfonic acid, formic acid, acetic acid, propionic acid, glycolic acid, pyruvic acid, oxylic acid, lactic acid, trifluoroacetic acid, citric acid, fumaric acid, maleic acid, malonic acid, tartaric acid, benzoic acid, cinnamic acid, mandelic acid, embonic acid, succinic acid or salicylic acid. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium, zinc, copper, manganese and aluminium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, histidine, caffeine, procaine, hydrabamine, choline, betaine, ethylendiamine, glucosamine, methylglucamine, theobromine, piperazine, N-ethylpiperidine, piperidine and polyamine resins. The compound of formula I can also be present in the form of zwitterions. Pharmaceutically acceptable salts of compounds of formula I of particular interest are the sodium salts or salts with tertiary amines.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

The term "agonist" denotes a compound that enhances the activity of another compound or receptor site as defined e.g. in Goodman and Gilman's "The Pharmacological Basis of Therapeutics, 7th ed." in page 35, Macmillan Publ. Company, Canada, 1985. A "full agonist" effects a full response whereas a "partial agonist" effects less than full activation even when occupying the total receptor population. An "inverse agonist" produces an effect opposite to that of an agonist, yet binds to the same receptor binding-site.

The term "half maximal effective concentration" ($EC_{50}$) denotes the plasma concentration of a particular compound required for obtaining 50% of the maximum of a particular effect in vivo.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgment of the attending medical or veterinary practitioner, and other factors.

In detail, the present invention relates to benzazepine-4-carboxamide compounds of the formula

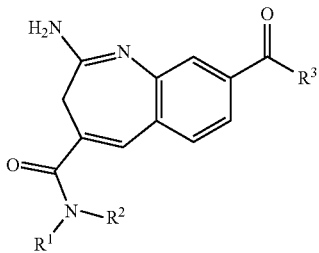

I wherein
$R^1$ is $C_{3-7}$-alkyl;
$R^2$ is $C_{3-7}$-alkyl or $C_{3-7}$-cycloalkyl-$C_{1-7}$-alkyl;
$R^3$ is a heterocycle selected from

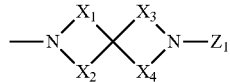

a)

wherein
$X_1$ is $(CH_2)_m$ wherein m is 1 or 2;
$X_2$ is $(CH_2)_n$ wherein n is 1 or 2;
$X_3$ is $(CH_2)_o$ wherein o is 1 or 2;
$X_4$ is $(CH_2)_p$ wherein p is 1 or 2; and
$Z_1$ is phenyl, wherein phenyl is unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl and di-$C_{1-7}$-alkyl-amino-$C_{1-7}$-alkyl; or

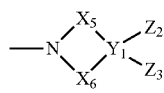

b)

wherein
$X_5$ is $(CH_2)_q$ wherein q is 1 or 2;
$X_6$ is $(CH_2)_r$ wherein r is 1 or 2;
$Y_1$ is a carbon or nitrogen atom and
$Z_2$ is hydrogen and
$Z_3$ is selected from the group consisting of hydrogen, $C_{1-7}$-alkoxy, $C_{2-7}$-alkenyloxy, phenyl, phenyl-$C_{1-7}$-alkyl, phenyl-$C_{1-7}$-alkyloxy, phenyl-$C_{1-7}$-alkylamino, phenylamino-$C_{1-7}$-alkyl, phenylamino, wherein phenyl is unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl and di-$C_{1-7}$-alkyl-amino-$C_{1-7}$-alkyl;

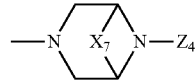

c)

wherein
$X_7$ is $(CH_2)_s$ wherein s is 1 or 2; and
$Z_4$ is phenyl, wherein phenyl is unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl and di-$C_{1-7}$-alkyl-amino-$C_{1-7}$-alkyl; or

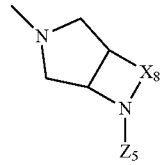

d)

wherein
$X_8$ is $(CH_2)_t$ wherein t is 1 or 2; and
$Z_5$ is phenyl, wherein phenyl is unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl and di-$C_{1-7}$-alkyl-amino-$C_{1-7}$-alkyl,
or pharmaceutically acceptable salts thereof.

In one aspect, $R^2$ is $C_{3-7}$-alkyl. In a particular aspect, $R^1$ and $R^2$ are n-propyl.

In another aspect, $R^2$ is $C_{3-7}$-cycloalkyl-$C_{1-7}$-alkyl. More particularly, $R^2$ is cyclopropylmethyl.

In one particular aspect, $R^2$ is n-propyl or cyclopropylmethyl. In another particular aspect $R^1$ is n-propyl.

In another aspect, provided are compounds of formula I, wherein $R^3$ has the formula a)

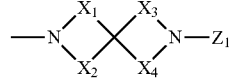

a)

wherein
$X_1$ is $(CH_2)_m$ wherein m is 1 or 2;
$X_2$ is $(CH_2)_n$ wherein n is 1 or 2;
$X_3$ is $(CH_2)_o$ wherein o is 1 or 2;
$X_4$ is $(CH_2)_p$ wherein p is 1 or 2; and
$Z_1$ is phenyl, wherein phenyl is unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl and di-$C_{1-7}$-alkyl-amino-$C_{1-7}$-alkyl.

In particular, $Z_1$ is phenyl or $C_{1-7}$-alkylphenyl.

In another particular aspect, m is 1 and n is 1. More particularly, m is 1, n is 1, o is 1 and p is 1. In another aspect, m is 1, n is 1, o is 2 and p is 2. In a further aspect, m is 1, n is 1, o is 2 and p is 1.

In a further aspect, m is 2 and n is 2. More particularly, m is 2, n is 2, o is 1 and p is 1.

In another aspect, provided are compounds of formula I, wherein $R^3$ has the formula b)

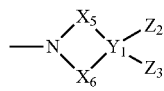

b)

wherein $X_5$ is $(CH_2)_q$ wherein q is 1 or 2;

$X_6$ is $(CH_2)_r$ wherein r is 1 or 2;

$Y_1$ is a carbon or nitrogen atom and $Z_2$ is hydrogen and $Z_3$ is selected from the group consisting of hydrogen, $C_{1-7}$-alkoxy, $C_{2-7}$-alkenyloxy, phenyl, phenyl-$C_{1-7}$-alkyl, phenyl-$C_{1-7}$-alkyloxy, phenyl-$C_{1-7}$-alkylamino, phenylamino-$C_{1-7}$-alkyl, phenylamino, wherein phenyl is unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl and di-$C_{1-7}$-alkyl-amino-$C_{1-7}$-alkyl.

In one aspect, provided are compounds of formula 1, wherein $Y_1$ is C.

In another aspect, provided are compounds of formula 1, wherein $Y_1$ is N.

In a further particular aspect, $Z_3$ is selected from the group consisting of phenyl, phenyl-$C_{1-7}$-alkyl, phenyl-$C_{1-7}$-alkyloxy, phenyl-$C_{1-7}$-alkyl amino, phenylamino-$C_{1-7}$-alkyl, phenylamino and amino-$C_{1-7}$-alkylphenyl. In another particular aspect, $Z_3$ is $C_{1-7}$-alkoxy or $C_{2-7}$-alkenyloxy.

In another particular aspect, q is 1 and r is 1. In another aspect, q is 2 and r is 2. In yet another particular aspect, q is 2 and r is 1.

In another aspect, provided are compounds of formula I, wherein $R^3$ has the formula c)

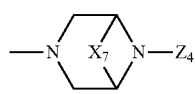

c)

wherein $X_7$ is $(CH_2)_s$ wherein s is 1 or 2; and $Z_4$ is phenyl, wherein phenyl is unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl and di-$C_{1-7}$-alkyl-amino-$C_{1-7}$-alkyl.

In a particular aspect, $Z_4$ is phenyl.

In another aspect, provided are compounds of formula I, wherein $R^3$ has the formula d)

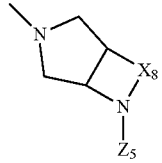

d)

wherein $X_5$ is $(CH_2)_t$ wherein t is 1 or 2; and $Z_5$ is phenyl, wherein phenyl is unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl and di-$C_{1-7}$-alkyl-amino-$C_{1-7}$-alkyl.

In a particular aspect, $Z_5$ is phenyl. In a further particular aspect, t is 1.

Particular compounds of formula I according to the invention are the following:

2-amino-N,N-dipropyl-8-[6-(p-tolyl)-2,6-diazaspiro[3.3]heptane-2-carbonyl]-3H-1-benzazepine-4-carboxamide, 2-amino-8-(4-anilinopiperidine-1-carbonyl)-N,N-dipropyl-3H-1-benzazepine-4-carboxamide, 2-amino-8-(3-anilinoazetidine-1-carbonyl)-N,N-dipropyl-3H-1-benzazepine-4-carboxamide, 2-amino-8-[3-(anilinomethyl)azetidine-1-carbonyl]-N,N-dipropyl-3H-1-benzazepine-4-carboxamide, 2-amino-8-(3-anilinopyrrolidine-1-carbonyl)-N,N-dipropyl-3H-1-benzazepine-4-carboxamide, 2-amino-8-(4-phenylpiperazine-1-carbonyl)-N,N-dipropyl-3H-1-benzazepine-4-carboxamide, 2-amino-8-(7-phenyl-2,7-diazaspiro[3.4]octane-2-carbonyl)-N,N-dipropyl-3H-1-benzazepine-4-carboxamide, 2-amino-N,N-dipropyl-8-(pyrrolidine-1-carbonyl)-3H-1-benzazepine-4-carboxamide, 2-amino-8-(4-anilinopiperidine-1-carbonyl)-N-(cyclopropylmethyl)-N-propyl-3H-1-benzazepine-4-carboxamide, 2-amino-8-(4-benzylpiperazine-1-carbonyl)-N,N-dipropyl-3H-1-benzazepine-4-carboxamide, 2-amino-8-(3-benzyloxyazetidine-1-carbonyl)-N,N-dipropyl-3H-1-benzazepine-4-carboxamide, 2-amino-8-(6-phenyl-3,6-diazabicyclo[3.1.1]heptane-3-carbonyl)-N,N-dipropyl-3H-1-benzazepine-4-carboxamide, 2-amino-8-(2-phenyl-2,7-diazaspiro[3.5]nonane-7-carbonyl)-N,N-dipropyl-3H-1-benzazepine-4-carboxamide, 2-amino-8-(7-phenyl-2,7-diazaspiro[3.5]nonane-2-carbonyl)-N,N-dipropyl-3H-1-benzazepine-4-carboxamide, 2-amino-8-(8-phenyl-3,8-diazabicyclo[3.2.1]octane-3-carbonyl)-N,N-dipropyl-3H-1-benzazepine-4-carboxamide, 2-amino-8-(6-phenyl-3,6-diazabicyclo[3.2.0]heptane-3-carbonyl)-N,N-dipropyl-3H-1-benzazepine-4-carboxamide, 2-amino-8-[3-(benzylamino)azetidine-1-carbonyl]-N,N-dipropyl-3H-1-benzazepine-4-carboxamide, 2-amino-8-[3-[4-(aminomethyl)anilino]pyrrolidine-1-carbonyl]-N,N-dipropyl-3H-1-benzazepine-4-carboxamide, 2-amino-8-[3-(benzylamino)pyrrolidine-1-carbonyl]-N,N-dipropyl-3H-1-benzazepine-4-carboxamide, 2-amino-8-[4-(anilinomethyl)piperidine-1-carbonyl]-N,N-dipropyl-3H-1-benzazepine-4-carboxamide, 2-amino-8-[3-(anilinomethyl)pyrrolidine-1-carbonyl]-N,N-dipropyl-3H-1-benzazepine-4-carboxamide, 2-amino-8-[3-[(E)-but-2-enoxy]azetidine-1-carbonyl]-N,N-dipropyl-3H-1-benzazepine-4-carboxamide,
2-amino-8-(3-anilinopiperidine-1-carbonyl)-N,N-dipropyl-3H-1-benzazepine-4-carboxamide,
2-amino-8-[3-(benzylamino)piperidine-1-carbonyl]-N,N-dipropyl-3H-1-benzazepine-4-carboxamide,
2-amino-8-(3-butoxyazetidine-1-carbonyl)-N,N-dipropyl-3H-1-benzazepine-4-carboxamide, and pharmaceutically acceptable salts thereof.

Particular compounds of formula I, wherein R³ has the formula a), are the following:
2-amino-N,N-dipropyl-8-[6-(p-tolyl)-2,6-diazaspiro[3.3]heptane-2-carbonyl]-3H-1-benzazepine-4-carboxamide,
2-amino-8-(7-phenyl-2,7-diazaspiro[3.4]octane-2-carbonyl)-N,N-dipropyl-3H-1-benzazepine-4-carboxamide,
2-amino-8-(2-phenyl-2,7-diazaspiro[3.5]nonane-7-carbonyl)-N,N-dipropyl-3H-1-benzazepine-4-carboxamide,
2-amino-8-(7-phenyl-2,7-diazaspiro[3.5]nonane-2-carbonyl)-N,N-dipropyl-3H-1-benzazepine-4-carboxamide,
and pharmaceutically acceptable salts thereof.

Particular compounds of formula I, wherein R³ has the formula b), are the following:
2-amino-8-(4-anilinopiperidine-1-carbonyl)-N,N-dipropyl-3H-1-benzazepine-4-carboxamide,
2-amino-8-(3-anilinoazetidine-1-carbonyl)-N,N-dipropyl-3H-1-benzazepine-4-carboxamide,
2-amino-8-[3-(anilinomethyl)azetidine-1-carbonyl]-N,N-dipropyl-3H-1-benzazepine-4-carboxamide,
2-amino-8-(3-anilinopyrrolidine-1-carbonyl)-N,N-dipropyl-3H-1-benzazepine-4-carboxamide,
2-amino-8-(4-phenylpiperazine-1-carbonyl)-N,N-dipropyl-3H-1-benzazepine-4-carboxamide,
2-amino-N,N-dipropyl-8-(pyrrolidine-1-carbonyl)-3H-1-benzazepine-4-carboxamide,
2-amino-8-(4-anilinopiperidine-1-carbonyl)-N-(cyclopropylmethyl)-N-propyl-3H-1-benzazepine-4-carboxamide,
2-amino-8-(4-benzylpiperazine-1-carbonyl)-N,N-dipropyl-3H-1-benzazepine-4-carboxamide,
2-amino-8-(3-benzyloxyazetidine-1-carbonyl)-N,N-dipropyl-3H-1-benzazepine-4-carboxamide,
2-amino-8-[3-(benzylamino)azetidine-1-carbonyl]-N,N-dipropyl-3H-1-benzazepine-4-carboxamide,
2-amino-8-[3-[4-(aminomethyl)anilino]pyrrolidine-1-carbonyl]-N,N-dipropyl-3H-1-benzazepine-4-carboxamide,
2-amino-8-[3-(benzylamino)pyrrolidine-1-carbonyl]-N,N-dipropyl-3H-1-benzazepine-4-carboxamide,
2-amino-8-[4-(anilinomethyl)piperidine-1-carbonyl]-N,N-dipropyl-3H-1-benzazepine-4-carboxamide,
2-amino-8-[3-(anilinomethyl)pyrrolidine-1-carbonyl]-N,N-dipropyl-3H-1-benzazepine-4-carboxamide,
2-amino-8-[3-[(E)-but-2-enoxy]azetidine-1-carbonyl]-N,N-dipropyl-3H-1-benzazepine-4-carboxamide,
2-amino-8-(3-anilinopiperidine-1-carbonyl)-N,N-dipropyl-3H-1-benzazepine-4-carboxamide,
2-amino-8-[3-(benzylamino)piperidine-1-carbonyl]-N,N-dipropyl-3H-1-benzazepine-4-carboxamide,
2-amino-8-(3-butoxyazetidine-1-carbonyl)-N,N-dipropyl-3H-1-benzazepine-4-carboxamide,
and pharmaceutically acceptable salts thereof.

Particular compounds of formula I, wherein R³ has the formula c), are the following:
2-amino-8-(6-phenyl-3,6-diazabicyclo[3.1.1]heptane-3-carbonyl)-N,N-dipropyl-3H-1-benzazepine-4-carboxamide,
2-amino-8-(8-phenyl-3,8-diazabicyclo[3.2.1]octane-3-carbonyl)-N,N-dipropyl-3H-1-benzazepine-4-carboxamide,
and pharmaceutically acceptable salts thereof.

A particular compound of formula I, wherein R³ has the formula d), is the following:
2-amino-8-(6-phenyl-3,6-diazabicyclo[3.2.0]heptane-3-carbonyl)-N,N-dipropyl-3H-1-benzazepine-4-carboxamide,
and pharmaceutically acceptable salts thereof.

A further aspect of the present invention is the process for the manufacture of compounds of formula I as defined above, which process comprises coupling a compound of the formula II

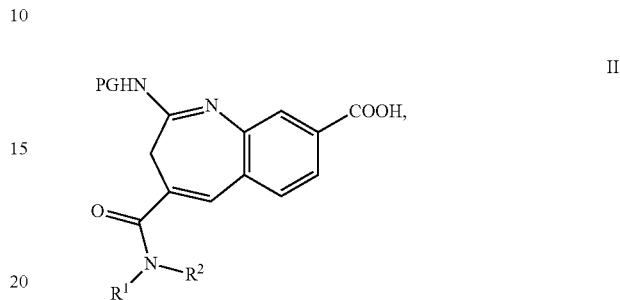

wherein R¹ and R² are as defined herein before and PG is a protecting group, with an amine of the formula III

R³H      III wherein R³ is defined herein before, under basic conditions in the presence of a coupling agent and removing the protecting group PG under acidic conditions to obtain a compound of the formula I

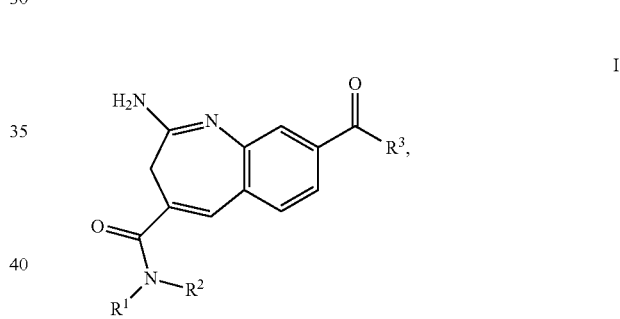

wherein R¹ to R³ are as defined herein before, and, if desired, converting the compound obtained into a pharmaceutically acceptable salt.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

In particular, a suitable protecting group PG is an amino-protecting group selected from Boc (tert-butoxycarbonyl), benzyl (Bz) and benzyloxycarbonyl (Cbz). In particular, the protecting group is Boc.

"Removing the protecting group PG under acidic conditions" means treating the protected compound with acids in a suitable solvent, for instance trifluoroacetic acid (TFA) in a solvent such as dichloromethane (DCM) can be employed.

A suitable "coupling agent" for the reaction of compounds of formula II with amines of formula III is selected from the group consisting of N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]

pyridinium-3-oxide hexafluorophosphate (HATU), 1-hydroxy-1,2,3-benzotriazole (HOBT), O-benzotriazole-N,N,N',N'-tetramethyl-uronium-hexafluoro-phosphate (HBTU) or O-benzotriazol-1-yl-N,N,N',N'-tetramethyluronium tetrafluoroborate (TBTU). In particular, the coupling agent is TBTU. Suitable bases include triethylamine, N-methylmorpholine and, particularly, diisopropylethyl amine.

"Under basic conditions" means the presence of a base, in particular a base selected from the group consisting of triethylamine, N-methylmorpholine and, particularly, diisopropylethylamine. Typically, the reaction is carried out in inert solvents such as dimethylformamide or dichloromethane at room temperature.

The invention further relates to compounds of formula I as defined above obtainable according to a process as defined above.

The compounds of the present invention can be prepared by any conventional means. Suitable processes for synthesizing these compounds as well as their starting materials are provided in the schemes below and in the examples. All substituents, in particular, $R^1$ to $R^4$ are as defined above unless otherwise indicated. Furthermore, and unless explicitly otherwise stated, all reactions, reaction conditions, abbreviations and symbols have the meanings well known to a person of ordinary skill in organic chemistry.

A general synthetic route for preparing the compounds of formula I is shown in Scheme 1 below.

Compounds of formula I can be prepared according to Scheme 1. A coupling reaction between carboxylic acid A and a selected amine IV gives the amide of formula V, which is then protected with an amino protecting group such as Boc to obtain a compound of formula VI. Hydrolysis of the compound of formula VI leads to a carboxylic acid of formula II. The carboxylic acid of formula II is then coupled with selected amines IIIa-d to obtain an amide of formula VII. Finally, the compound of formula I is obtained by deprotection of the amino protecting group (e.g. Boc). In some cases, the compound of formula VII may contain an additional acid labile protection group originated from amine IV or amine III, like Boc or TBS, which will be removed also in the final deprotection step.

A coupling reagent, like HBTU, is used to couple the carboxylic acid of formula A and a selected amine IV in the presence of a base, like DIPEA, in a solvent like DCM at ambient or elevated temperature to give a compound of formula V.

Then, the compound of formula V is protected with an amino protecting group, in particular with Boc, to provide a compound of formula VI.

The compound of formula VI is hydrolyzed by a base, in particular LiOH, in a suitable solvent, for example a mixed solvent like THF/MeOH/H$_2$O, at ambient or elevated temperature to obtain a carboxylic acid of formula II.

Scheme 1

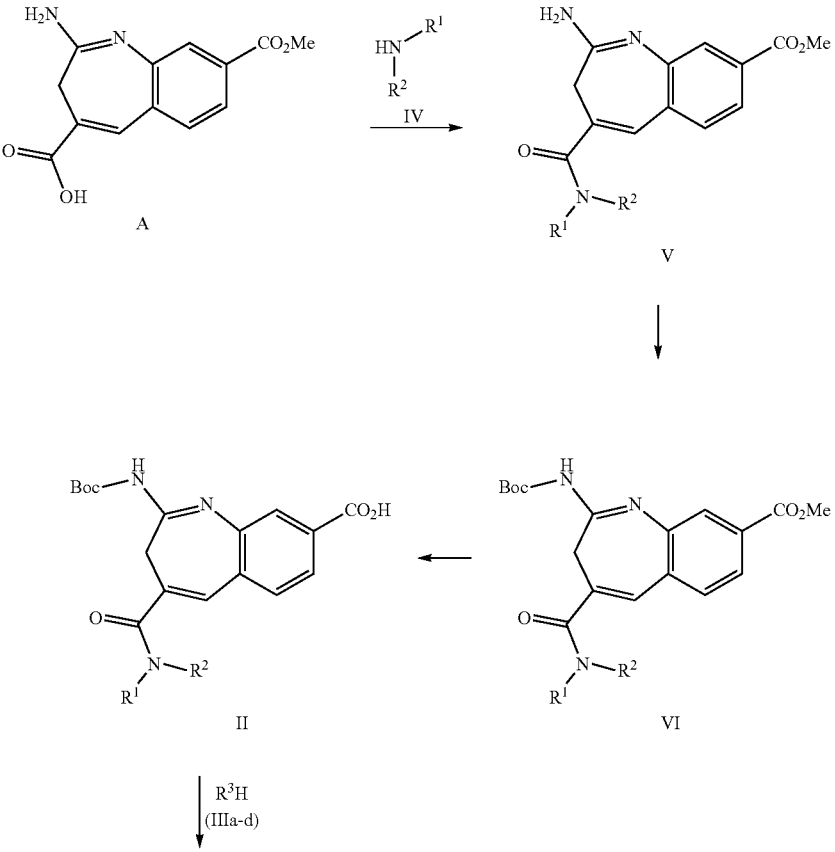

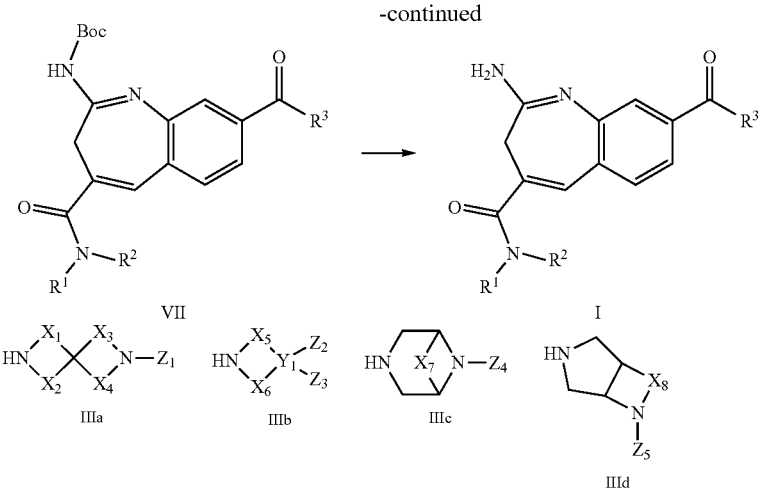

The carboxylic acid of formula II is then reacted with a selected amine IIIa-d under the assistance of a suitable coupling reagent, in particular HBTU, in a solvent like DCM and in the presence of a base, in particular DIPEA, at ambient or elevated temperature to result in a compound of formula VII.

Finally, a compound of formula I is obtained by deprotecting the compound of formula VII with TFA in dichloromethane and subsequent purification by prep-HPLC. In some cases, besides the Boc protection group at amidine, a compound of formula VII may also contain an additional acid labile protection group, like Boc or TBS originated from amine IV or III, which will be also removed in this step.

If one of the starting materials contains one or more functional groups which are not stable or are reactive under the reaction conditions of one or more reaction steps, appropriate protecting groups (PG) (as described e.g. in T. W. Greene et al., Protective Groups in Organic Chemistry, John Wiley and Sons Inc. New York 1999, 3rd edition) can be introduced before the critical step applying methods well known in the art. Such protecting groups can be removed at a later stage of the synthesis using standard methods known in the art. In some cases, besides the Boc protection group at amidine, a compound of formula VII may also contain an additional acid labile protection group, like Boc or TBS originated from amine II or VI, which will be also removed in this step.

If one or more compounds of the formula contain chiral centers, compounds of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

As described herein before, the compounds of formula I of the present invention can be used as medicaments for the treatment of diseases which are mediated by TLR agonists, in particular for the treatment of diseases which are mediated by TLR8 agonists.

The compounds defined in the present invention are agonists of TLR8 receptors in cellular assays in vitro. Accordingly, the compounds of the present invention are expected to be potentially useful agents in the treatment of diseases or medical conditions that may benefit from the activation of the immune system via TLR8 agonists. They are useful in the treatment or prevention of diseases such as cancer, autoimmune diseases, inflammation, sepsis, allergy, asthma, graft rejection, graft-versus-host disease, immunodeficiencies, and infectious diseases.

In more detail, the compounds of formula I of the present invention are useful in oncology, i.e. they may be used in the treatment of common cancers including bladder cancer, head and neck cancer, prostate cancer, colorectal cancer, kidney cancer, breast cancer, lung cancer, ovarian cancer, cervical cancer, liver cancer, pancreatic cancer, bowel and colon cancer, stomach cancer, thyroid cancer, melanoma, skin and brain tumors and malignancies affecting the bone marrow such as leukemias and lymphoproliferative systems, such as Hodgkin's and non-Hodgkin's lymphoma; including the prevention (e.g. vaccination) and treatment of metastatic cancer and tumor recurrences, and paraneoplastic syndromes.

The compounds of formula I of the present invention are also useful in the treatment of autoimmune diseases. An "autoimmune disease" is a disease or disorder arising from and directed against an individual's own tissues or organs or a co-segregate or manifestation thereof or resulting condition therefrom. "Autoimmune disease" can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease which can affect multiple organ systems (for example, systemic lupus erythematosus (SLE), rheumatoid arthritis, polymyositis, etc.). In a particular aspect, the autoimmune disease is associated with the skin, muscle tissue, and/or connective tissue.

Particular autoimmune diseases include autoimmune rheumatologic disorders (such as, for example, rheumatoid arthritis, Sjogren's syndrome, scleroderma, lupus such as SLE and lupus nephritis, polymyositis/dermatomyositis, cryoglobulinemia, anti-phospholipid antibody syndrome, and psoriatic arthritis), autoimmune gastrointestinal and liver disorders (such as, for example, inflammatory bowel diseases, ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)), allergic conditions and responses, food allergies, drug allergies, insect allergies, rare allergic disorders such as mastocytosis, allergic reaction, eczema including allergic or atopic eczema, asthma such as bronchial asthma and autoimmune asthma, conditions involving infiltration of myeloid cells and T cells and chronic inflammatory responses:

The compounds of formula I of the present invention are also useful in the treatment of infectious diseases. Thus, they may be useful in the treatment of viral diseases, in particular for diseases caused by infection with viruses selected from the group consisting of papilloma viruses, such as human papilloma virus (HPV) and those that cause genital warts, common warts and plantar warts, herpes simplex virus (HSV), molluscum contagiosum, hepatitis B virus (HBV), hepatitis C virus (HCV), Dengue virus, variola virus, human immunodeficiency virus (HIV), cytomegalovirus (CMV), varicella zoster virus (VZV), rhinovirus, enterovirus, adenovirus, coronavirus (e.g. SARS), influenza, mumps and parainfluenza.

They may also be useful in the treatment of bacterial diseases, in particular for diseases caused by infection with bacteria selected from the group consisting of *mycobacterium* such as *mycobacterium tuberculosis, mycobacterium avium* and *mycobacterium leprae*. The compounds of formula I of the present invention may further be useful in the treatment of other infectious diseases, such as *chlamydia*, fungal diseases, in particular fungal diseases selected from the group consisting of candidiasis, aspergillosis and cryptococcal meningitis, and parasitic diseases such as *Pneumocystis carnii*, pneumonia, cryptosporidiosis, histoplasmosis, toxoplasmosis, trypanosome infection and leishmaniasis.

Thus, the expression "diseases which are mediated by TLR agonists" means diseases which may be treated by activation of the immune system with TLR8 agonists such as cancer, autoimmune diseases, inflammation, sepsis, allergy, asthma, graft rejection, graft-versus-host disease, immunodeficiencies, and infectious diseases. In particular, the expression "diseases which are mediated by TLR agonists" means cancer, autoimmune diseases, inflammation, sepsis, allergy, asthma, graft rejection, graft-versus-host disease, immunodeficiencies, and infectious diseases.

In a particular aspect, the expression "which are mediated by TLR agonists" relates to cancer selected from the group consisting of bladder cancer, head and neck cancer, liver cancer, prostate cancer, colorectal cancer, kidney cancer, breast cancer, lung cancer, ovarian cancer, cervical cancer, pancreatic cancer, bowel and colon cancer, stomach cancer, thyroid cancer, melanoma, skin and brain tumors and malignancies affecting the bone marrow such as leukemias and lymphoproliferative systems, such as Hodgkin's and non-Hodgkin's lymphoma; including the prevention (e.g. vaccination) and treatment of metastatic cancer and tumor recurrences, and paraneoplastic syndromes.

The invention also relates to pharmaceutical compositions comprising a compound of formula I as defined above and a pharmaceutically acceptable carrier and/or adjuvant. More specifically, the invention relates to pharmaceutical compositions useful for the treatment of diseases which are which are mediated by TLR agonists.

Further, the invention relates to compounds of formula I as defined above for use as therapeutically active substances, particularly as therapeutically active substances for the treatment of diseases which are which are mediated by TLR agonists. In particular, the invention relates to compounds of formula I for use in the treatment of cancers or autoimmune diseases or infectious diseases selected from the group consisting of viral diseases, bacterial diseases, fungal diseases and parasitic diseases.

In another aspect, the invention relates to a method for the treatment a of diseases which are mediated by TLR agonists, which method comprises administering a therapeutically active amount of a compound of formula I to a human being or animal. In particular, the invention relates to a method for the treatment of cancers and infectious diseases selected from the group consisting of viral diseases, bacterial diseases, fungal diseases and parasitic diseases.

The invention further relates to the use of compounds of formula I as defined above for the treatment of diseases which are mediated by TLR agonists.

In addition, the invention relates to the use of compounds of formula I as defined above for the preparation of medicaments for the treatment of diseases which are mediated by TLR agonists. In particular, the invention relates to the use of compounds of formula I as defined above for the preparation of medicaments for the treatment of cancers or autoimmune diseases or infectious diseases selected from the group consisting of viral diseases, bacterial diseases, fungal diseases and parasitic diseases.

In a further aspect, compounds of formula I can be in combination with one or more additional treatment modalities in a regimen for the treatment of cancer.

Combination therapy encompasses, in addition to the administration of a compound of the invention, the adjunctive use of one or more modalities that are effective in the treatment of cancer. Such modalities include, but are not limited to, chemotherapeutic agents, immunotherapeutics, anti-angiogenic agents, cytokines, hormones, antibodies, polynucleotides, radiation and photodynamic therapeutic agents. In a specific aspect, combination therapy can be used to prevent the recurrence of cancer, inhibit metastasis, or inhibit the growth and/or spread of cancer or metastasis. As used herein, "in combination with" means that the compound of formula I is administered as part of a treatment regimen that comprises one or more additional treatment modalities as mentioned above. The invention thus also relates to a method for the treatment of cancer, which method comprises administering a therapeutically active amount of a compound of formula I in combination with one or more other pharmaceutically active compounds to a human being or animal.

Compounds of formula I can be used alone or in combination with one or more additional treatment modalities in treating autoimmune diseases.

Combination therapy encompasses, in addition to the administration of a compound of the invention, the adjunctive use of one or more modalities that aid in the prevention or treatment of autoimmune diseases. Such modalities include, but are not limited to, chemotherapeutic agents, immunotherapeutics, anti-angiogenic agents, cytokines, hormones, antibodies, polynucleotides, radiation and photodynamic therapeutic agents. As used herein, "in combination with" means that the compound of formula I is administered as part of a treatment regimen that comprises one or more additional treatment modalities as mentioned above. The invention thus also relates to a method for the treatment of autoimmune diseases, which method comprises administering a therapeutically active amount of a compound of formula I in combination with one or more other pharmaceutically active compounds to a human being or animal.

In a further aspect, compounds of formula I can be used alone or in combination with one or more additional treatment modalities in treating infectious diseases.

Combination therapy encompasses, in addition to the administration of a compound of the invention, the adjunctive use of one or more modalities that aid in the prevention or treatment of infectious diseases. Such modalities include, but are not limited to, antiviral agents, antibiotics, and anti-fungal agents. As used herein, "in combination with" means that the compound of formula I is administered as part of a treatment regimen that comprises one or more additional treatment modalities as mentioned above. The invention thus also relates to a method for the treatment of infectious diseases, which method comprises administering a therapeutically active amount of a compound of formula I in combination with one or more other pharmaceutically active compounds to a human being or animal.

Pharmacological Test

The following tests were carried out in order to determine the activity of the compounds of formula I:

For TLR8 and TLR7 activity testing, HEK-Blue human TLR8 or TLR7 cells (Invivogen, San Diego, Calif., USA) are used, respectively. These cells are designed for studying the stimulation of human TLR8 or TLR7 by monitoring the activation of NF-κB. A SEAP (secreted embryonic alkaline phosphatase) reporter gene is placed under the control of the IFN-b minimal promoter fused to five NF-κB and AP-1-binding sites. Therefore the reporter expression is regulated by the NF-κB promoter upon stimulation of human TLR8 or TLR7 for 20 hours. The cell culture supernatant SEAP reporter activity was determined using Quanti Blue kit (Invivogen, San Diego, Ca, USA) at a wavelength of 640 nm, a detection medium that turns purple/blue in the presence of alkaline phosphatase. $EC_{50}$ values were determined using Activity Base analysis (ID Business Solution, Limited).

The compounds according to formula I have an activity ($EC_{50}$ value) in the above assay for human TLR8 in the range of 0.001 μM to 0.05 μM, more particularly of 0.001 μM to 0.03 μM, whereas the activity ($EC_{50}$ value) in the above assay for human TLR7 is greater than 0.1 μM, in the range of 0.4 μM to >100 μM, meaning the compounds show high selectivity towards human TLR8.

For example, the following compounds showed the following $EC_{50}$ values in the assay described above:

| Example | human TLR8 $EC_{50}$ [μM] | human TLR7 $EC_{50}$ [μM] |
|---|---|---|
| 1 | 0.005 | >100 |
| 2 | 0.006 | 7.9 |
| 3 | 0.005 | 24 |
| 4 | 0.01 | 10 |
| 5 | 0.004 | 14 |
| 6 | 0.025 | 9 |
| 7 | 0.01 | >100 |
| 8 | 0.015 | 21 |
| 9 | 0.02 | 18 |
| 10 | 0.005 | 14 |
| 11 | 0.004 | 15 |
| 12 | 0.022 | 11 |
| 13 | 0.007 | >100 |
| 14 | 0.009 | 33 |
| 15 | 0.01 | 16 |
| 16 | 0.029 | 12 |
| 17 | 0.018 | 17 |
| 18 | 0.031 | >100 |
| 19 | 0.014 | 6.6 |
| 20 | 0.02 | 10 |
| 21 | 0.009 | 6.98 |
| 22 | 0.012 | 32 |
| 23 | 0.008 | 0.4 |
| 24 | 0.014 | 3.1 |
| 25 | 0.008 | 31.1 |

Pharmaceutical Compositions

The compounds of formula I and their pharmaceutically acceptable salts can be used as medicaments, e.g., in the form of pharmaceutical preparations for enteral, parenteral or topical administration. The compounds of formula I and their pharmaceutically acceptable salts may be administered by systemic (e.g., parenteral) or local (e.g., topical or intralesional injection) administration. In some instances, the pharmaceutical formulation is topically, parenterally, orally, vaginally, intrauterine, intranasal, or by inhalation administered. As described herein, certain tissues may be preferred targets for the TLR agonist. Thus, administration of the TLR agonist to lymph nodes, spleen, bone marrow, blood, as well as tissue exposed to virus, are preferred sites of administration.

In one aspect, the pharmaceutical formulation comprising the compounds of formula I or its pharmaceutically acceptable salts is administered parenterally. Parenteral routes of administration include, but are not limited to, transdermal, transmucosal, nasopharyngeal, pulmonary and direct injection. Parenteral administration by injection may be by any parenteral injection route, including, but not limited to, intravenous (IV), including bolus and infusion (e.g., fast or slow), intraperitoneal (IP), intramuscular (IM), subcutaneous (SC) and intradermal (ID) routes. Transdermal and transmucosal administration may be accomplished by, for example, inclusion of a carrier (e.g., dimethylsulfoxide, DMSO), by application of electrical impulses (e.g., iontophoresis) or a combination thereof. A variety of devices are available for transdermal administration which may be used. Formulations of the compounds of formula I suitable for parenteral administration are generally formulated in USP water or water for injection and may further comprise pH buffers, salts bulking agents, preservatives, and other pharmaceutically acceptable excipients.

Transdermal administration is accomplished by application of a cream, rinse, gel, etc. capable of allowing the TLR agonist to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference. Transdermal transmission may also be accomplished by iontophoresis, for example using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter. Administration via the transdermal and transmucosal routes may be continuous or pulsatile.

Pulmonary administration is accomplished by inhalation, and includes delivery routes such as intranasal, transbronchial and transalveolar routes. Formulations of compounds of formula I suitable for administration by inhalation including, but not limited to, liquid suspensions for forming aerosols as well as powder forms for dry powder inhalation delivery systems are provided. Devices suitable for administration by inhalation include, but are not limited to, atomizers, vaporizers, nebulizers, and dry powder inhalation delivery devices. Other methods of delivering to respiratory mucosa include delivery of liquid formulations, such as by nose drops. Administration by inhalation is preferably accomplished in discrete doses (e.g., via a metered dose inhaler), although delivery similar to an infusion may be accomplished through use of a nebulizer.

The compounds of formula I and pharmaceutically acceptable salts thereof may also be administered orally, e.g., in the form of tablets, coated tablets, dragees, hard and soft gelatine capsules.

The production of the pharmaceutical preparations can be effected in a manner which will be familiar to any person skilled in the art by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1-500 mg, preferably 1-100 mg, of a compound of formula I.

The following examples $C_1$ to $C_3$ illustrate typical compositions of the present invention, but serve merely as representative thereof.

Example C1

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example C2

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C3

Injection solutions can have the following composition:

| | |
|---|---|
| Compound of formula I | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

The following examples serve to illustrate the present invention in more detail. They are, however, not intended to limit its scope in any manner.

EXAMPLES

Abbreviations Used Therein

Boc$_2$O=di-tert-butyl dicarbonate, Boc=t-butyl carbamate, calc'd=calculated, CD$_3$OD=deuterated methanol, d=day, DIPEA=N,N-diisopropylethylamine, DCM=dichloromethane, DMAP: 4-dimethylaminopyridine, DMF-DMA: N,N-dimethylformamide dimethyl acetal, EA=ethyl acetate or EtOAc, EC$_{50}$=half maximal effective concentration, EDCI=1-(3-dimethylaminopropyl)-3-ethylcarbodiimide hydrochloride, h or hr=hour, HOBT=N-hydroxybenzotriazole, HBTU=O-(benzotriazol-1-yl)-N,N,N',N'-tetramethyluronium hexafluorophosphate, HATU: (1-[bis(dimethylamino)methylene]-1H-1,2,3-triazolo[4,5-b]pyridinium 3-oxid hexafluorophosphate), Pa$_2$dba$_3$: tris(dibenzylideneacetone)dipalladium(0), TBAI=N,N,N-tributyl-1-butanaminiuiodide, HPLC=high performance liquid chromatography, HPLC-UV=high performance liquid chromatography with ultraviolet detector, Hz=hertz, mg=milligram, MHz=megahertz, min=minute(s), mL=milliliter, mm=millimeter, mM=mmol/L, mmol=millimole, MS=mass spectrometry, MW=molecular weight, NMR=nuclear magnetic resonance, PE=petroleum ether, prep-HPLC=preparative high performance liquid chromatography, rt=room temperature, sat.=sat., TBS=tert-butyldimethylsilyl, sxt=sextet, TEA=triethylamine, TFA=trifluoroacetic acid, THF=tetrahydrofuran, M=micromole/L, m=micrometer, UV=ultraviolet detector, OD=optical density, Pd(dppf)$_2$Cl$_2$=[1,1'-Bis(diphenylphosphino)-ferrocene]dichloropalladium(II), TLR8=toll-like receptor 8, TLR7=toll-like receptor 7, NF-κB=nuclear factor kappa-light-chain-enhancer of activated B cells, SEAP=secreted embryonic alkaline phosphatase, IFN-3=interferon-beta.

Example A—Preparation of Key Intermediate A

2-Amino-8-methoxycarbonyl-3H-1-benzazepine-4-carboxylic acid

A detailed synthetic route is provided in Scheme 2.

a) Preparation of Compound B

To a solution of methyl 4-methyl-3-nitrobenzoate (100 g, 0.51 mol) in DMF (1 L) was added DMF-DMA (73 g, 0.61 mol). The reaction mixture was heated to 105° C. for 18 hrs. Then the solvent was removed in vacuo to give methyl 4-(2-(dimethylamino)vinyl)-3-nitrobenzoate (compound B, 127 g, crude) which was used in the next step without purification. MS: calc'd 251 (M+H)$^+$, measured 251 (M+H)$^+$.

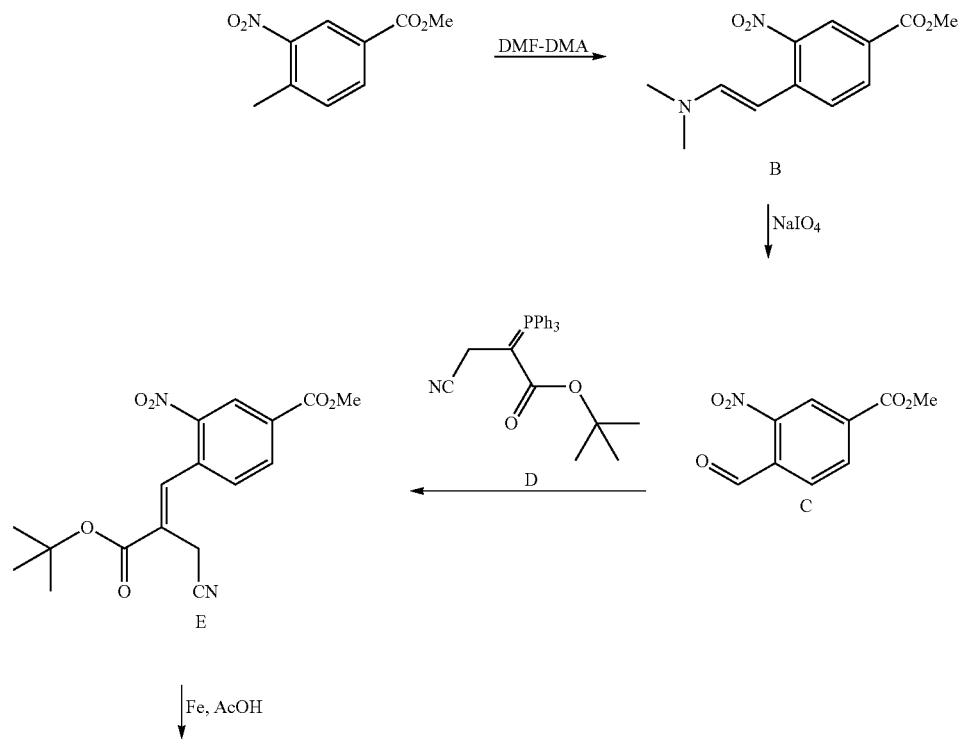

Scheme 2

-continued

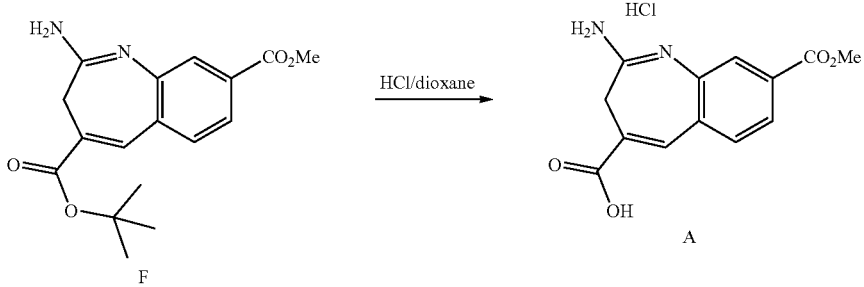

b) Preparation of Compound C

To a solution of NaIO$_4$ (327 g, 1.53 mol) in a mixed solvent of THF (1.3 L) and water (2.0 L) was added a THF (0.7 L) solution of methyl 4-(2-(dimethylamino)vinyl)-3-nitrobenzoate (compound A, 127 g, 0.51 mol) at 10° C. After the reaction mixture was stirred at 25° C. for 18 hrs, the mixture was filtered and then extracted with EA. The organic layer was washed with brine, dried over anhydrous Na$_2$SO$_4$, filtered and concentrated to give the crude product. The crude product was purified by silica gel column chromatography (PE:EA=20:1-10:1) to give methyl 4-formyl-3-nitrobenzoate (compound C, 84 g, 79%) as a yellow solid. MS: calc'd 210 (M+H)$^+$, measured 210 (M+H)$^+$.

c) Preparation of Compound D

To a solution of tert-butyl 2-(triphenylphosphoranylidene)acetate (300 g, 0.797 mol) in EA (2 L) was added 2-bromoacetonitrile (57 g, 0.479 mol) at 25° C. The reaction was heated to reflux for 18 hrs. After it was cooled to ambient temperature, the solid was filtered and the filtrate was concentrated. The residue was purified by triturating from EA and PE (200 mL, 2.5:1) to give the desired product tert-butyl 3-cyano-2-(triphenylphosphoranylidene)propanoate (compound D, 125 g, 63%) as a white solid. MS: calc'd 416 (M+H)$^+$, measured 416 (M+H)$^+$.

d) Preparation of Compound E

To a solution of 4-formyl-3-nitrobenzoate (compound C, 50 g, 0.24 mol) in toluene (600 mL) was added tert-butyl 3-cyano-2-(triphenylphosphoranylidene)propanoate (compound D, 109 g, 0.26 mol) at 25° C. After the reaction mixture was stirred at 25° C. for 18 hrs, it was cooled in ice-bath for 1 hr. The precipitate was collected and dried to give the desired product as a white solid. The filtrate was concentrated and treated with EtOH (120 mL). The undissolved material was filtered and the filtrate was concentrated to give an additional batch of the desired product. These two batches were combined to give methyl 4-(3-(tert-butoxy)-2-(cyanomethyl)-3-oxoprop-1-en-1-yl)-3-nitrobenzoate (compound E, 60 g, 72%). MS: calc'd 347 (M+H)$^+$, measured 347 (M+H)$^+$.

e) Preparation of Compound F

To a solution of methyl 4-(3-(tert-butoxy)-2-(cyanomethyl)-3-oxoprop-1-en-1-yl)-3-nitrobenzoate (compound E, 30 g, 87 mmol) in AcOH (450 mL) was added Fe powder (29.1 g, 520 mmol) at 60° C. After the reaction mixture was heated at 85° C. for 3 hrs, it was filtered through celite and the precipitate was washed with acetic acid. The filtrate was concentrated in vacuo and the residue was carefully basified with aqueous sat. NaHCO$_3$ solution (300 mL). Then EA (600 mL) was added. The mixture was filtered through celite and the precipitate was washed with EA (200 mL). The filtrate was then washed with water, dried over Na$_2$SO$_4$ and concentrated in vacuo to get 4-tert-butyl 8-methyl 2-amino-3H-benzo[b]azepine-4,8-dicarboxylate (compound F, 25 g, 93%) as a light yellow solid. MS: calc'd 317 (M+H)$^+$, measured 317 (M+H)$^+$.

f) Preparation of Compound A

To a solution of 4-tert-butyl 8-methyl 2-amino-3H-benzo[b]azepine-4,8-dicarboxylate (compound F, 25 g, 80 mmol) in dioxane (400 mL) was added a 1 M solution of HCl in dioxane (600 mL) at 0° C. After the reaction mixture was stirred at 25° C. for 18 hrs, it was concentrated in vacuo to give 2-amino-8-(methoxycarbonyl)-3H-benzo[b]azepine-4-carboxylic acid hydrochloride (compound A, 25 g, crude) which was used in the next step without any purification. MS: calc'd 261 (M+H)$^+$, measured 261 (M+H)$^+$.

Example B—Preparation of Key Intermediate J 2-(tert-butoxycarbonylamino)-4-(dipropylcarbamoyl)-3H-1-benzazepine-8-carboxylic acid A detailed synthetic route is provided in Scheme 3.

g) Preparation of Compound G

To a mixture of 2-amino-8-(methoxycarbonyl)-3H-benzo[b]azepine-4-carboxylic acid hydrochloride (compound A, 19 g, 64 mmol), HBTU (29 g, 77 mmol), DIPEA (33 g, 257 mmol) in DMF (400 mL) was added di-n-propylamine (13 g, 128 mmol) at 0° C. After the reaction mixture was stirred at 20° C. for 2 hrs, it was quenched with sat. NH$_4$Cl (500 mL), diluted with H$_2$O (1 L), and extracted with EA (300 mL×3). The combined organic layers were washed with brine (300 mL×2), dried over Na$_2$SO$_4$ and concentrated to give the crude product. The crude product was purified by silica gel silica gel column chromatography (PE:EA=1:1) to give methyl 2-amino-4-(dipropylcarbamoyl)-3H-benzo[b]azepine-8-carboxylate (compound G, 18 g, 82%) as a yellow solid. MS: calc'd 344 (M+H)$^+$, measured 344 (M+H)$^+$.

Scheme 3

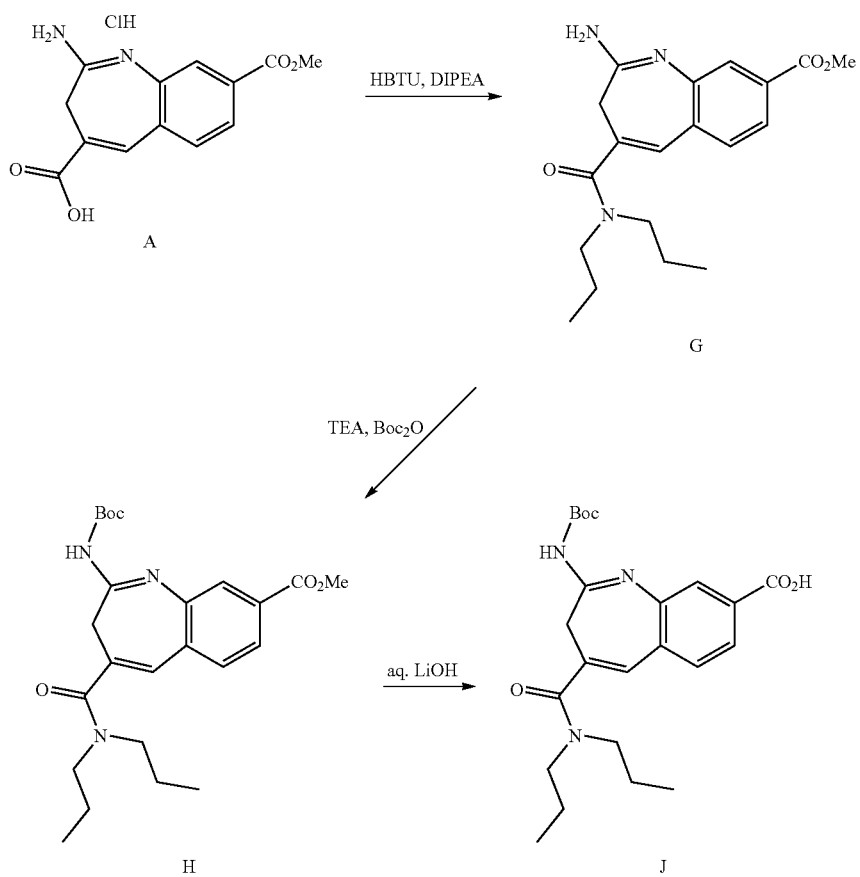

h) Preparation of Compound H

To a mixture of methyl 2-amino-4-(dipropylcarbamoyl)-3H-benzo[b]azepine-8-carboxylate 5 (compound G, 18 g, 53 mmol) and TEA (16 g, 157 mmol) in DCM (300 mL) was added Boc$_2$O (17 g, 79 mmol) at 0° C. After the mixture was stirred at 20° C. for 16 hrs, it was quenched with sat. NH$_4$Cl (300 mL), diluted with H$_2$O (500 mL), and extracted with DCM (100 mL×3). The combined organic layers were washed with brine (100 mL×2), dried over Na$_2$SO$_4$ and concentrated to give the crude product. The crude product was purified by silica gel column chromatography (PE: EA=3:1) to give methyl 2-((tert-butoxycarbonyl)amino)-4-(dipropylcarbamoyl)-3H-benzo[b]azepine-8-carboxylate (compound H, 21 g, yield: 91%) as a yellow solid. MS: calc'd 444 (M+H)$^+$, measured 444 (M+H)$^+$.

i) Preparation of Compound J

To a solution of methyl 2-((tert-butoxycarbonyl)amino)-4-(dipropylcarbamoyl)-3H-benzo[b]azepine-8-carboxylate (compound H, 5.0 g, 11.3 mmol) in THF/H$_2$O (1/1, 100 mL) was added aq. LiOH solution (1 M, 17 mL, 17 mmol) at 0° C. Then the mixture was warmed to 25° C. and stirred for 6 hrs. The mixture was poured into ice-water (150 mL), acidified with aq. citric acid (5%) to pH=5 and extracted with EtOAc (100 mL×3). The combined organic layers were washed with brine (100 mL×2), dried over Na$_2$SO$_4$ and concentrated in vacuo to give 2-(tert-butoxycarbonylamino)-4-(dipropylcarbamoyl)-3H-1-benzazepine-8-carboxylic acid (compound J, 4.0 g, 83.3%) as a yellow solid. $^1$H NMR (400 MHz, DMSO-d$_6$) δ ppm=7.78-7.72 (m, 1H), 7.64 (dd, J=1.5, 8.0 Hz, 1H), 7.55 (d, J=8.3 Hz, 1H), 6.93-6.89 (m, 1H), 3.14 (s, 6H), 1.54 (br. s., 4H), 1.44 (s, 9H), 0.80 (br. s., 6H). MS: calc'd 430 (M+H)$^+$, measured 430 (M+H)$^+$.

Example 1

2-Amino-N,N-dipropyl-8-[6-(p-tolyl)-2,6-diazaspiro[3.3]heptane-2-carbonyl]-3H-1-benzazepine-4-carboxamide

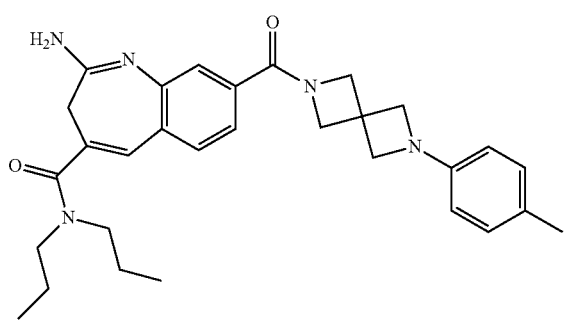 [SMILES: CCCN(CCC)C(=O)C1=Cc2ccc(C(=O)N3CC4(C3)CN(c3ccc(C)cc3)C4)cc2N=C(N)C1]

Example 1 can be prepared according to general procedure in scheme 1. A detailed synthetic route is provided in Scheme 4.

Scheme 4

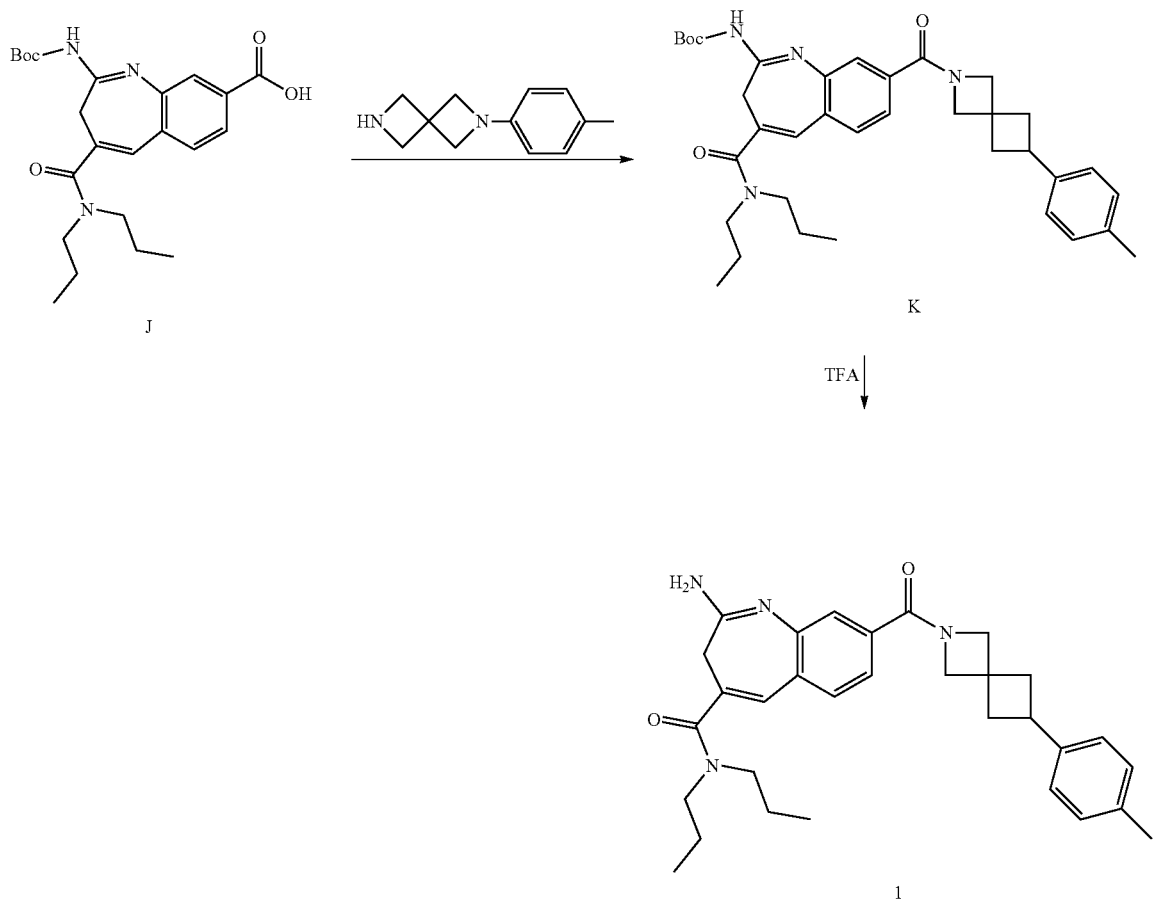

Preparation of Example 1

To a solution of 2-(tert-butoxycarbonylamino)-4-(dipropylcarbamoyl)-3H-benzo[b]azepine-8-carboxylic acid (compound J, 50 mg, 116 µmol), DIPEA (45 mg, 349 µmol) and 2-(p-tolyl)-2,6-diazaspiro[3.3]heptane (22 mg, 116 µmol) in DCM (5 mL) was added HATU (88 mg, 233 µmol) at r.t. The mixture was stirred at r.t. overnight. After the reaction was completed, water was added. Then the mixture was extracted with DCM. The organic layer was concentrated to give the crude intermediate K. The crude intermediate K was dissolved into DCM (3 mL) and then TFA (0.3 mL) was added at rt. The reaction was stirred at rt for 2 hrs. The solvent was removed on vacuo and the residue was purified by prep-HPLC to give the desired product (Example 1, 5 mg) as a white solid. $^1$HNMR (400 MHz, METHANOL-$d_4$) δ ppm=7.54-7.77 (m, 3H), 6.94-7.13 (m, 3H), 6.46 (d, J=8.3 Hz, 2H), 4.62 (s, 2H), 4.39 (s, 2H), 3.81-4.09 (m, 4H), 3.38-3.59 (m, 4H), 3.21 (m, 2H), 2.11-2.29 (s, 3H), 1.71 (sxt, J=7.4 Hz, 4H), 0.96 ppm (m, 6H). MS: calc'd 500 $(M+H)^+$, measured 500 $(M+H)^+$.

Example 2

2-Amino-8-(4-anilinopiperidine-1-carbonyl)-N,N-dipropyl-3H-1-benzazepine-4-carboxamide

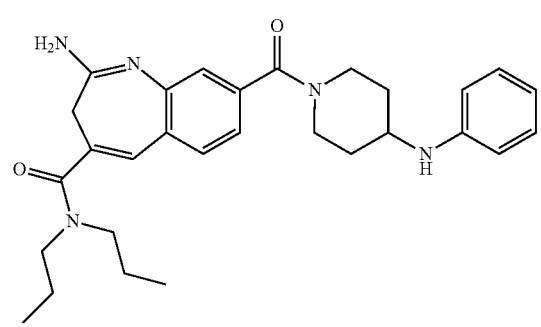 [SMILES: CCCN(CCC)C(=O)C1=Cc2ccc(C(=O)N3CCC(Nc4ccccc4)CC3)cc2N=C(N)C1]

The title compound was prepared in analogy to Example 1 by using N-phenylpiperidin-4-amine hydrochloride instead of 2-(p-tolyl)-2,6-diazaspiro[3.3]heptane. Example 2 was obtained as a white solid (31 mg). $^1$H NMR (400 MHz, METHANOL-$d_4$) δ ppm=7.52 (d, J=8 Hz, 1H), 7.29 (s, 1H), 7.26 (dd, J=8 Hz, 4 Hz, 1H), 7.10 (t, J=8 Hz, 2H), 6.96 (s, 1H), 6.68 (d, J=8 Hz, 2H), 6.62 (t, J=8 Hz, 1H), 4.54-4.51 (m, 1H), 3.79-3.76 (m, 1H), 3.65-3.58 (m, 1H), 3.45-3.42 (m, 4H), 3.31 (s, 2H), 3.30 (m, 1H), 3.16-3.13 (m, 1H), 2.13-2.02 (m, 2H), 1.73-1.63 (m, 4H), 1.49-1.41 (m, 2H), 0.93 (br, 6H). MS: calc'd 488 (M+H)$^+$, measured 488 (M+H)$^+$.

Example 3

2-Amino-8-(3-anilinoazetidine-1-carbonyl)-N,N-dipropyl-3H-1-benzazepine-4-carboxamide

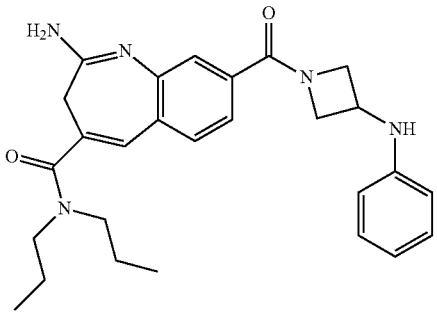 [SMILES: CCCN(CCC)C(=O)C1=Cc2ccc(C(=O)N3CC(Nc4ccccc4)C3)cc2N=C(N)C1]

The title compound was prepared in analogy to Example 1 by using N-phenylazetidin-3-amine (Compound 3D) instead of 2-(p-tolyl)-2,6-diazaspiro[3.3]heptane. Example 3 was obtained as a white solid (20 mg). $^1$H NMR (400 MHz, METHANOL-$d_4$) δ ppm=7.69 (s, 3H), 7.19-7.12 (m, 2H), 7.11-7.07 (m, 1H), 6.74-6.68 (m, 1H), 6.63-6.57 (m, 2H), 4.80-4.73 (m, 1H), 4.64-4.55 (m, 1H), 4.46-4.36 (m, 1H), 4.23-4.16 (m, 1H), 4.09-4.02 (m, 1H), 3.54-3.43 (m, 4H), 3.36 (br. s., 2H), 1.78-1.64 (m, 4H), 1.07-0.84 (m, 6H). MS: calc'd 460 (M+H)$^+$, measured 460 (M+H)$^+$.

Preparation of Compound 3D:

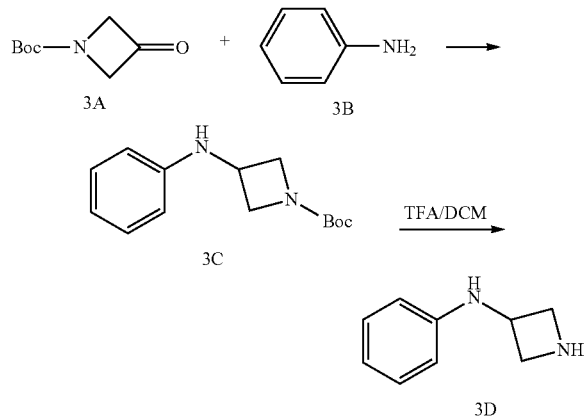

To a solution of tert-butyl 3-oxoazetidine-1-carboxylate (compound 3A, 2.0 g, 11.7 mmol) and aniline (compound 3B, 1.3 g, 14.0 mmol) in DCM (60 mL) was added AcOH (0.8 g, 14.0 mmol), Ti(Oi-Pr)$_4$ (4.0 g, 14.0 mmol) and NaBH(OAc)$_3$ (3.0 g, 14.0 mmol) at 0° C. After the reaction was heated at 40° C. for 18 hrs, 10 mL of aq. NaOH (2 M) was added to the solution at 0° C. The precipitate was filtered and the filtrate was concentrated. The residue was purified by triturating with methyl tert-butyl ether (10 mL) to give the desired product tert-butyl 3-(phenylamino)azetidine-1-carboxylate (compound 3C, 1.5 g, 51.7%) as a white solid. MS: calc'd 249 (M+H)$^+$, measured 249 (M+H)$^+$.

To a solution of tert-butyl 3-(phenylamino)azetidine-1-carboxylate (compound 3C, 0.5 g, 2.1 mmol) in DCM (7.5 mL) was added TFA (4.0 g, 40.3 mmol) at 0° C. The reaction was stirred at 20° C. for 3 hrs. The solvent was removed on vacuo and the residue was purified by triturating from methyl tert-butyl ether (15 mL) to give the desired product N-phenylazetidin-3-amine (compound 3D, 0.4 g, 76.9%) as a white solid. MS: calc'd 149 (M+H)$^+$, measured 149 (M+H)$^+$.

Example 4

2-Amino-8-[3-(anilinomethyl)azetidine-1-carbonyl]-N,N-dipropyl-3H-1-benzazepine-4-carboxamide

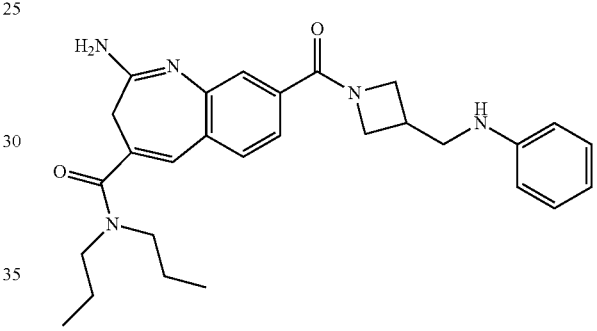

The title compound was prepared in analogy to Example 1 by using N-(azetidin-3-ylmethyl)aniline (Compound 4B) instead of 2-(p-tolyl)-2,6-diazaspiro[3.3]heptane. Example 4 was obtained as a white solid (40 mg). $^1$H NMR (400 MHz, METHANOL-$d_4$) δ ppm=7.58-7.55 (m, 3H), 7.10 (t, J=8 Hz, 2H), 7.00 (s, 1H), 6.66-6.60 (m, 3H), 4.49 (t, J=8 Hz, 1H), 4.30 (t, J=8 Hz, 1H), 4.17-4.14 (m, 1H), 3.97-3.93 (m, 1H), 3.44 (t, J=8 Hz, 4H), 3.36 (d, J=4 Hz, 2H), 3.31 (s, 2H), 3.06-2.99 (m, 1H), 1.71-1.65 (m, 4H), 0.93 (br, 6H). MS: calc'd 474 (M+H)$^+$, measured 474 (M+H)$^+$.

Preparation of Compound 4B:

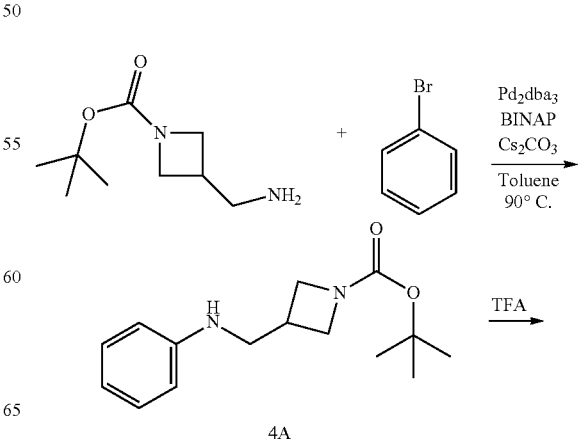

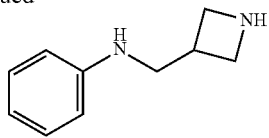

4B

To a tube was added tert-butyl 3-(aminomethyl)azetidine-1-carboxylate (186 mg, 182 μl, 999 mol), bromobenzene (188 mg, 125 μl, 1.2 mmol), toluene (4 mL), 2,2'-bis(diphenylphosphino)-1,1'-binaphthalene (62 mg, 100 μmol), $Cs_2CO_3$ (651 mg, 2 mmol) and $Pd_2(dba)_3$ (46 mg, 50 μmol). Then it was bubbled with $N_2$ for 5 mins and heated to 90° C. (oil bath) for about 13.5 hours. The reaction mixture was filtered through a layer of celite, and the celite was washed with toluene and EA. The filtrate was concentrated to give a brown oil which was purified by silica gel column chromatography (eluted with EA/PE=0-20%-40%), about 83 mg tert-butyl 3-(anilinomethyl)azetidine-1-carboxylate (Compound 4A) was obtained as a yellow oil. MS: calc'd 263 $(M+H)^+$, measured 263 $(M+H)^+$.

Compound 4A was dissolved in DCM (2 mL) and cooled with ice bath. TFA (1 mL) was added. The mixture was warmed to rt and stirred for 2 hrs. The mixture was concentrated to give N-(azetidin-3-ylmethyl)aniline (Compound 4B) as a brown oil which was used directly in the next step. MS: calc'd 163 $(M+H)^+$, measured 163 $(M+H)^+$.

Example 5

2-Amino-8-(3-anilinopyrrolidine-1-carbonyl)-N,N-dipropyl-3H-1-benzazepine-4-carboxamide

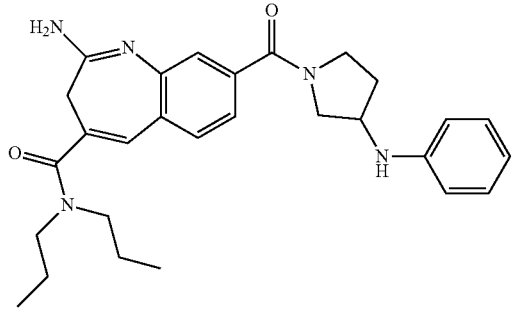 [SMILES: CCCN(CCC)C(=O)C1=Cc2ccc(C(=O)N3CCC(Nc4ccccc4)C3)cc2N=C(N)C1]

The title compound was prepared in analogy to Example 1 by using N-phenylpyrrolidin-3-amine (compound 5A) instead of 2-(p-tolyl)-2,6-diazaspiro[3.3]heptane. Example 5 was obtained as a yellow solid (17 mg). $^1$H NMR (400 MHz, METHANOL-$d_4$) δ ppm=7.65-7.47 (m, 3H), 7.24-7.19 (m, 1H), 7.08-7.04 (m, 2H), 6.79-6.61 (m, 3H), 4.22-4.20 (m, 0.5H), 4.10-4.09 (m, 0.5H), 3.95-3.90 (m, 0.5H), 3.88-3.75 (m, 1H), 3.75-3.68 (m, 1H), 3.65-3.55 (m, 1H), 3.50-3.35 (m, 4.5H), 3.33 (s, 2H), 2.36-2.25 (m, 1H), 2.08-2.03 (m, 1H), 1.72-1.65 (m, 4H), 0.97-0.9 (br. d., 6H). MS: calc'd 474 $(M+H)^+$, measured 474 $(M+H)^+$.

Preparation of Compound 5A

The title compound was prepared in analogy to compound 3D of Example 3 by using tert-butyl 3-oxopyrrolidine-1-carboxylate instead of tert-butyl 3-oxoazetidine-1-carboxylate.

Example 6

2-Amino-8-(4-phenylpiperazine-1-carbonyl)-N,N-dipropyl-3H-1-benzazepine-4-carboxamide

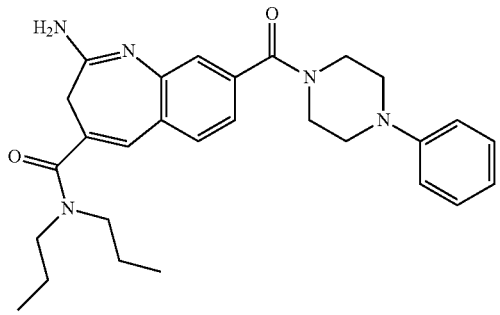 [SMILES: CCCN(CCC)C(=O)C1=Cc2ccc(C(=O)N3CCN(c4ccccc4)CC3)cc2N=C(N)C1]

The title compound was prepared in analogy to Example 1 by using 1-phenylpiperazine instead of 2-(p-tolyl)-2,6-diazaspiro[3.3]heptane. Example 6 was obtained as a white solid (24 mg). $^1$H NMR (400 MHz, METHANOL-$d_4$) δ ppm=7.50-7.65 (m, 1H), 7.18-7.42 (m, 4H), 6.97-7.09 (m, 3H), 6.80-6.95 (m, 1H), 3.94 (br. s., 2H), 3.66 (br. s., 2H), 3.46 (t, J=7.3 Hz, 4H), 3.01-3.31 (m, 6H), 1.70 (dq, J=14.9, 7.3 Hz, 4H), 0.95 (d, J=15.1 Hz, 6H). MS: calc'd 474 $(M+H)^+$, measured 474 $(M+H)^+$.

Example 7

2-Amino-8-(7-phenyl-2,7-diazaspiro[3.4]octane-2-carbonyl)-N,N-dipropyl-3H-1-benzazepine-4-carboxamide

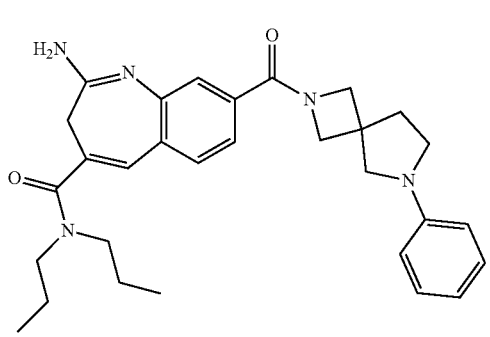 [SMILES: CCCN(CCC)C(=O)C1=Cc2ccc(C(=O)N3CC4(CCN(c5ccccc5)C4)C3)cc2N=C(N)C1]

The title compound was prepared in analogy to Example 1 by using 6-phenyl-2,6-diazaspiro[3.4]octane (compound 7A) instead of 2-(p-tolyl)-2,6-diazaspiro[3.3]heptane. Example 7 was obtained as a white solid (20 mg). $^1$H NMR (400 MHz, METHANOL-$d_4$) δ ppm=7.73-7.69 (m, 2H), 7.67-7.63 (m, 1H), 7.22-7.16 (m, 2H), 7.08 (s, 1H), 6.70-6.59 (m, 3H), 4.48-4.38 (m, 2H), 4.27-4.18 (m, 2H), 3.56 (s, 2H), 3.47 (s, 4H), 3.43-3.37 (m, 2H), 3.38 (s, 2H), 2.35-2.30 (t, J=6.80 Hz, 2H), 1.75-1.64 (m, 4H), 1.06-0.84 (m, 6H). MS: calc'd 500 $(M+H)^+$, measured 500 $(M+H)^+$.

Preparation of Compound 7A

The title compound was prepared in analogy to compound 4B of Example 4 by using tert-butyl 2,6-diazaspiro[3.4]octane-2-carboxylate instead of tert-butyl 3-(aminomethyl)azetidine-1-carboxylate.

Example 8

2-Amino-N,N-dipropyl-8-(pyrrolidine-1-carbonyl)-3H-1-benzazepine-4-carboxamide

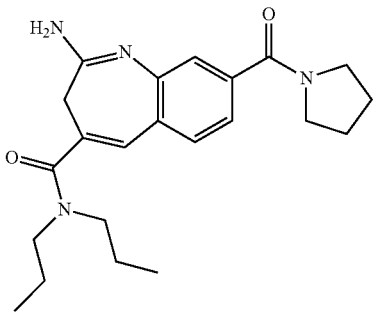 [SMILES: CCCN(CCC)C(=O)C1=Cc2ccc(C(=O)N3CCCC3)cc2N=C(N)C1]

The title compound was prepared in analogy to Example 1 by using pyrrolidine instead of 2-(p-tolyl)-2,6-diazaspiro[3.3]heptane. Example 8 was obtained as a white solid (7 mg). $^1$H NMR (400 MHz, METHANOL-$d_4$) δ ppm=7.39-7.68 (m, 3H), 7.07 (s, 1H), 3.64 (t, J=6.9 Hz, 2H), 3.37-3.55 (m, 8H), 1.85-2.11 (m, 4H), 1.71 (sxt, J=7.5 Hz, 4H), 0.95 (br., 6H). MS: calc'd 383 (M+H)$^+$, measured 383 (M+H)$^+$.

Example 9

2-Amino-8-(4-anilinopiperidine-1-carbonyl)-N-(cyclopropylmethyl)-N-propyl-3H-1-benzazepine-4-carboxamide

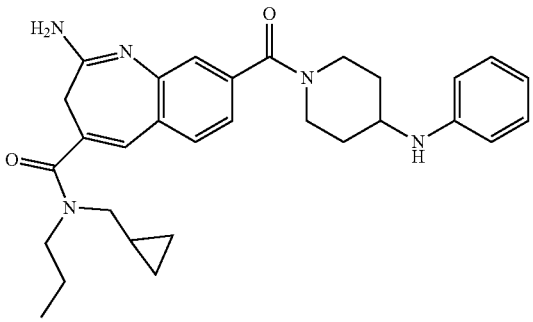 [SMILES: CCCN(CC1CC1)C(=O)C1=Cc2ccc(C(=O)N3CCC(Nc4ccccc4)CC3)cc2N=C(N)C1]

The title compound was prepared in analogy to Example 1 by using N-phenylpiperidin-4-amine hydrochloride and 2-(tert-butoxycarbonylamino)-4-[cyclopropylmethyl(propyl)-carbamoyl]-3H-1-benzazepine-8-carboxylic acid (compound 9A) instead of 2-(p-tolyl)-2,6-diazaspiro[3.3]heptane and 2-(tert-butoxycarbonylamino)-4-(dipropylcarbamoyl)-3H-benzo[b]azepine-8-carb oxylic acid (compound J). Example 9 was obtained as a white solid (12 mg). $^1$H NMR (400 MHz, METHANOL-$d_4$) δ ppm=7.63 (d, J=8 Hz, 1H), 7.45 (d, J=8 Hz, 1H), 7.42 (s, 1H), 7.26-7.24 (m, 2H), 7.09 (s, 1H), 6.92 (m, 3H), 4.59 (br, 1H), 3.77 (m, 1H), 3.70 (m, 1H), 3.56 (t, J=8 Hz, 2H), 3.40 (d, J=8 Hz, 2H), 3.36 (s, 2H), 3.14-3.13 (m, 2H), 2.14 (m, 1H), 2.01 (m, 1H), 1.75-1.68 (m, 2H), 1.59-1.49 (m, 2H), 1.09 (br, 1H), 0.95 (br, 3H), 0.61 (d, J=8 Hz, 2H), 0.29 (br, 2H). MS: calc'd 500 (M+H)$^+$, measured 500 (M+H)$^+$.

Preparation of Compound 9A
The title compound was prepared in analogy to Example B by using N-(cyclopropylmethyl)propan-1-amine instead of di-N-propylamine.

Example 10

2-Amino-8-(4-benzylpiperazine-1-carbonyl)-N,N-dipropyl-3H-1-benzazepine-4-carboxamide

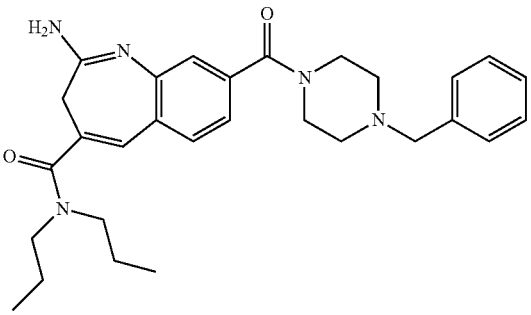 [SMILES: CCCN(CCC)C(=O)C1=Cc2ccc(C(=O)N3CCN(Cc4ccccc4)CC3)cc2N=C(N)C1]

The title compound was prepared in analogy to Example 1 by using 1-benzylpiperazine (Compound 10B) instead of 2-(p-tolyl)-2,6-diazaspiro[3.3]heptane. Example 10 was obtained as a white solid (8 mg). $^1$H NMR (400 MHz, METHANOL-$d_4$) δ ppm=7.67-7.64 (m, 1H), 7.54-7.49 (m, 7H), 7.07 (s, 1H), 4.39 (s, 2H), 3.84-3.78 (m, 4H), 4.45 (br, 4H), 3.40-3.35 (m, 4H), 3.33 (s, 2H), 1.74-1.64 (m, 4H), 0.93 (br, 6H). MS: calc'd 488 (M+H)$^+$, measured 488 (M+H)$^+$.

Preparation of Compound 10B:

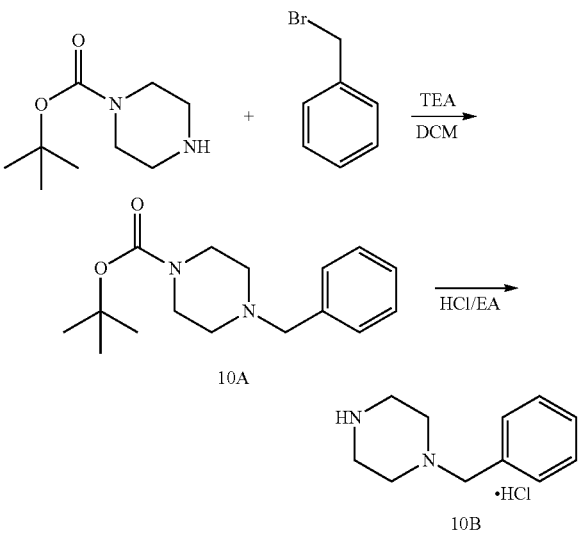

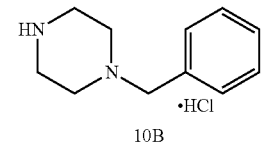

To a 25 mL flask was added TEA (177 mg, 244 µl, 1.75 mmol), tert-butyl piperazine-1-carboxylate (240 mg, 1.29 mmol), (bromomethyl)benzene (200 mg, 139 µl, 1.17 mmol) and DCM (4 mL). The colorless solution was stirred at rt for 3 hrs. The reaction mixture was concentrated to give a white solid. Then it was purified by silica gel column chromatography (eluted with EA/PE=15-30%), about 177 mg tert-butyl 4-benzylpiperazine-1-carboxylate (Compound 10A) was obtained as a colorless oil. MS: calc'd 277 (M+H)$^+$, measured 277 (M+H)$^+$.

Compound 10A was treated with 30 mL EA solution of HCl (1 M) and stirred at rt for 18.5 hrs. The mixture was concentrated in vacuo to give about 135 mg of 1-benzylpiperazine (Compound 10B) as a white solid which was used directly in the next step. MS: calc'd 177 (M+H)$^+$, measured 177 (M+H)$^+$.

Example 11

2-Amino-8-(3-benzyloxyazetidine-1-carbonyl)-N,N-dipropyl-3H-1-benzazepine-4-carboxamide

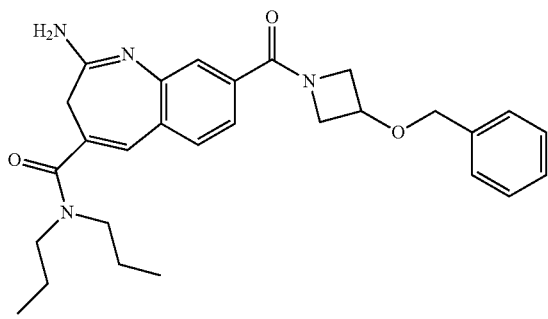 [SMILES: CCCN(CCC)C(=O)C1=Cc2ccc(C(=O)N3CC(OCc4ccccc4)C3)cc2N=C(N)C1]

The title compound was prepared in analogy to Example 1 by using 3-benzyloxyazetidine (Compound 11B) instead of 2-(p-tolyl)-2,6-diazaspiro[3.3]heptane. Example 11 was obtained as a white solid (8 mg). $^1$H NMR (400 MHz, METHANOL-$d_4$) δ ppm=7.64-7.61 (m, 3H), 7.38-7.29 (m, 5H), 7.06 (s, 1H), 4.56-4.49 (m, 4H), 4.39-4.35 (m, 1H), 4.28-4.26 (m, 1H), 4.06-4.02 (m, 1H), 3.45 (br, 4H), 3.34 (s, 2H), 1.74-1.64 (m, 4H), 0.93 (br, 6H). MS: calc'd 474 (M+H)$^+$, measured 474 (M+H)$^+$.

Preparation of Compound 11B:

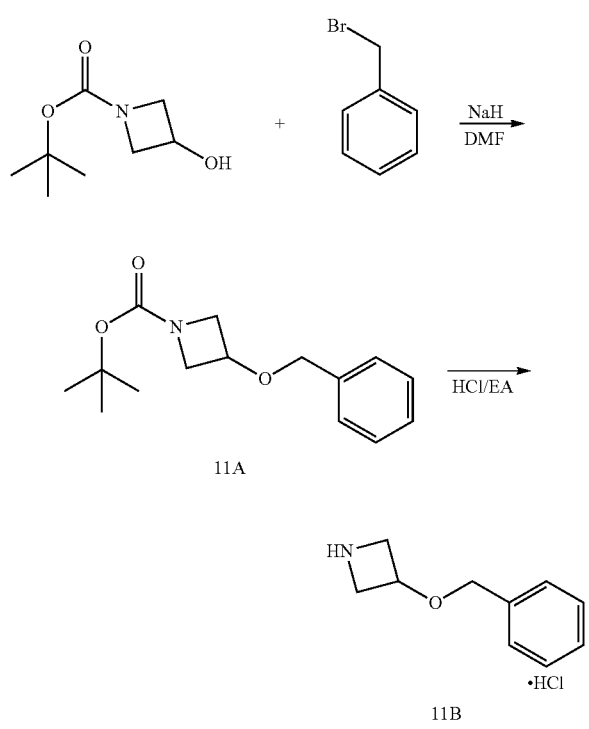

To a 25 mL flask was added tert-butyl 3-hydroxyazetidine-1-carboxylate (506 mg, 2.92 mmol) and DMF (5 mL). The solution was cooled to 0° C. and NaH (193 mg, 4.82 mmol) was added portion-wise. The reaction mixture was warmed to rt for 30 mins. Then it was cooled to 0° C. again and a solution of (bromomethyl)benzene (500 mg, 347 μl, 2.92 mmol) in 2 mL DMF was added. The reaction mixture was warmed to rt and stirred for 2 hrs. After the reaction was completed, the reaction mixture was quenched with sat. NH$_4$Cl, diluted with 25 mL of water and extracted with EA (25 mL×2). The combined organic layers were washed with sat. NH$_4$Cl (25 mL×2) and brine (25 mL). The separated organic layer was dried over Na$_2$SO$_4$ and concentrated to give 0.9 g yellow oil. The oil was purified by silica gel column chromatography (eluted with EA/PE=10-30%) to give 660 mg tert-butyl 3-benzyloxyazetidine-1-carboxylate (Compound 11A) as a colorless oil. MS: calc'd 264 (M+H)$^+$, measured 264 (M+H)$^+$.

Compound 11A was treated with 25 mL EA solution of HCl (1 M) and the mixture was stirred at rt for 6 hrs. The solvent was concentrated in vacuo to give about 410 mg of crude 3-benzyloxyazetidine (Compound 11B) as a colorless oil which was used directly in the next step. MS: calc'd 164 (M+H)$^+$, measured 164 (M+H)$^+$.

Example 12

2-Amino-8-(6-phenyl-3,6-diazabicyclo[3.1.1]heptane-3-carbonyl)-N,N-dipropyl-3H-1-benzazepine-4-carboxamide

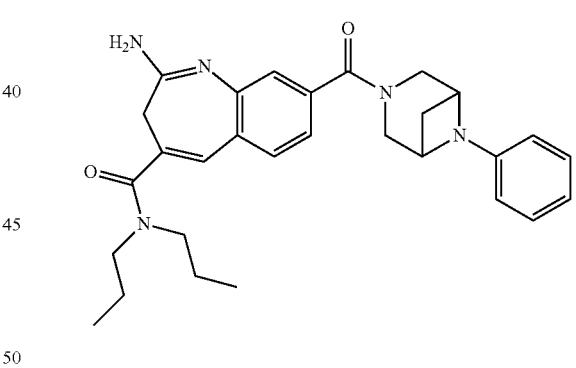

The title compound was prepared in analogy to Example 1 by using 6-phenyl-3, 6-diazabicyclo [3.1.1]heptane (compound 12A) instead of 2-(p-tolyl)-2,6-diazaspiro[3.3]heptane. Example 12 was obtained as a white solid (44 mg). $^1$H NMR (400 MHz, DMSO-$d_6$) δ ppm=7.59 (br. s., 1H), 7.46-7.52 (m, 2H), 7.13-7.24 (m, 2H), 6.97 (br. s., 1H), 6.63 (d, J=6.78 Hz, 3H), 4.61 (br. s., 1H), 3.57-3.72 (m, 2H), 3.31-3.41 (m, 7H), 3.22 (d, J=9.03 Hz, 2H), 2.03 (br. s., 2H), 1.61 (qd, J=7.32, 14.68 Hz, 4H), 0.88 (t, J=7.34 Hz, 6H). MS: calc'd 486.3 (M+H)$^+$, measured 486.3 (M+H)$^+$.

Preparation of Compound 12A:

The title compound was prepared in analogy to compound 4B of Example 4 by using tert-butyl 3, 6-diazabicyclo [3.1.1] heptane-3-carboxylate instead of tert-butyl 3-(aminomethyl)azetidine-1-carboxylate.

Example 13

2-Amino-8-(2-phenyl-2,7-diazaspiro[3.5]nonane-7-carbonyl)-N,N-dipropyl-3H-1-benzazepine-4-carboxamide

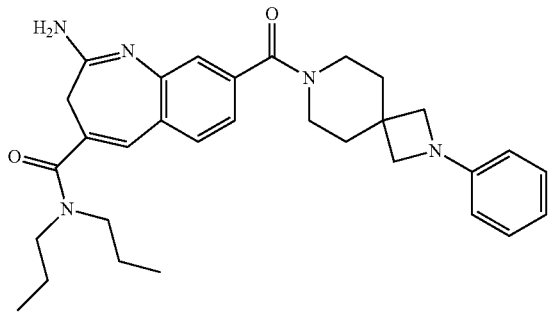 [SMILES: CCCN(CCC)C(=O)C1=Cc2ccc(C(=O)N3CCC4(CC3)CN(c3ccccc3)C4)cc2N=C(N)C1]

The title compound was prepared in analogy to Example 1 by using 2-phenyl-2,7-diazaspiro[3.5]nonane (compound 13A) instead of 2-(p-tolyl)-2,6-diazaspiro[3.3]heptane. Example 13 was obtained as a light-yellow solid (64 mg). $^1$H NMR (400 MHz, METHANOL-$d_4$) δ ppm=7.67-7.63 (d, J=8.40 Hz, 1H), 7.48-7.44 (m, 2H), 7.33-7.27 (t, J=8.40 Hz, 2H), 7.07 (s, 1H), 6.97-6.91 (t, J=7.20 Hz, 1H), 6.82-6.78 (d, J=7.20 Hz, 2H), 3.92 (br. s., 4H), 3.80 (br. s, 2H), 3.47 (br. s, 6H), 3.38 (s, 2H), 2.00 (s, 2H), 1.92 (s, 2H), 1.76-1.64 (m, 4H), 1.07-0.82 (br. s, 6H). MS: calc'd 514 (M+H)$^+$, measured 514 (M+H)$^+$.

Preparation of Compound 13A:

The title compound was prepared in analogy to compound 4B of Example 4 by using tert-butyl 2,7-diazaspiro[3.5]nonane-7-carboxylate instead of tert-butyl 3-(aminomethyl)azetidine-1-carboxylate.

Example 14

2-Amino-8-(7-phenyl-2,7-diazaspiro[3.5]nonane-2-carbonyl)-N,N-dipropyl-3H-1-benzazepine-4-carboxamide

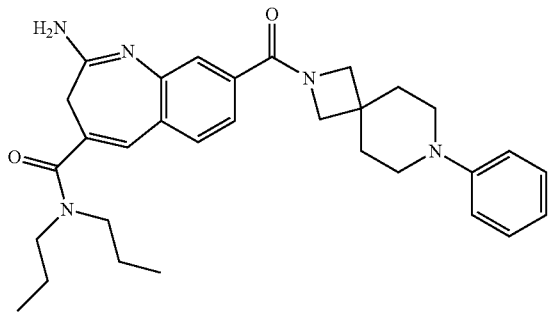 [SMILES: CCCN(CCC)C(=O)C1=Cc2ccc(C(=O)N3CC4(CCN(c5ccccc5)CC4)C3)cc2N=C(N)C1]

The title compound was prepared in analogy to Example 1 by using 7-phenyl-2,7-diazaspiro[3.5]nonane (compound 14A) instead of 2-(p-tolyl)-2,6-diazaspiro[3.3]heptane. Example 14 was obtained as a white solid (45.7 mg). $^1$H NMR (400 MHz, METHANOL-$d_4$) δ ppm=7.75 (s, 1H), 7.73-7.70 (m, 1H), 7.69-7.65 (m, 1H), 7.63-7.54 (m, 4H), 7.51-7.46 (m, 1H), 7.09 (s, 1H), 4.35 (s, 2H), 4.11 (s, 2H), 3.68-3.57 (m, 4H), 3.47 (br. s, 4H), 3.38 (s, 2H), 2.35-2.26 (m, 4H), 1.76-1.66 (m, 4H), 1.07-0.82 (br. s, 6H). MS: calc'd 514 (M+H)$^+$, measured 514 (M+H)$^+$.

Preparation of Compound 14A:

The title compound was prepared in analogy to compound 4B of Example 4 by using tert-butyl 2,7-diazaspiro[3.5]nonane-2-carboxylate instead of tert-butyl 3-(aminomethyl)azetidine-1-carboxylate.

Example 15

2-Amino-8-(8-phenyl-3,8-diazabicyclo[3.2.1]octane-3-carbonyl)-N,N-dipropyl-3H-1-benzazepine-4-carboxamide

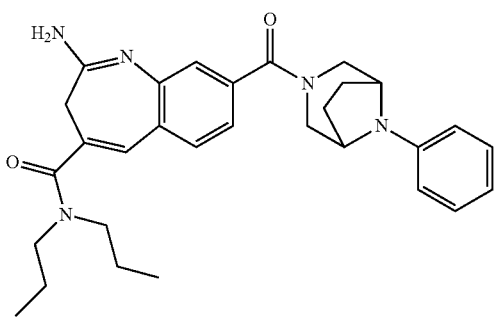 [SMILES: CCCN(CCC)C(=O)C1=Cc2ccc(C(=O)N3CC4CCC(C3)N4c3ccccc3)cc2N=C(N)C1]

The title compound was prepared in analogy to Example 1 by using 8-phenyl-3,8-diazabicyclo[3.2.1]octane (compound 15A) instead of 2-(p-tolyl)-2,6-diazaspiro[3.3]heptane. Example 15 was obtained as a white solid (31.2 mg). $^1$H NMR (400 MHz, METHANOL-$d_4$) δ ppm=7.67-7.62 (d, J=8.40 Hz, 1H), 7.45-7.40 (m, 2H), 7.29-7.23 (m, 2H), 7.07 (s, 1H), 6.96-6.62 (d, J 8.00 Hz, 2H), 6.82-6.77 (t, J=7.60 Hz, 1H), 4.47-4.35 (m, 2H), 4.24 (s, 1H), 3.75-3.65 (d, J=12.40 Hz, 1H), 3.47 (s, 4H), 3.41-3.34 (m, 4H), 2.15-1.90 (m, 3H), 1.82-1.75 (m, 1H), 1.75-1.65 (m, 4H), 1.06-0.87 (br, s, 6H). MS: calc'd 500 (M+H)$^+$, measured 500 (M+H)$^+$.

Preparation of Compound 15A:

The title compound was prepared in analogy to compound 4B of Example 4 by using tert-butyl 3,8-diazabicyclo[3.2.1]octane-3-carboxylate instead of tert-butyl 3-(aminomethyl)azetidine-1-carboxylate.

Example 16

2-Amino-8-(6-phenyl-3,6-diazabicyclo[3.2.0]heptane-3-carbonyl)-N,N-dipropyl-3H-1-benzazepine-4-carboxamide

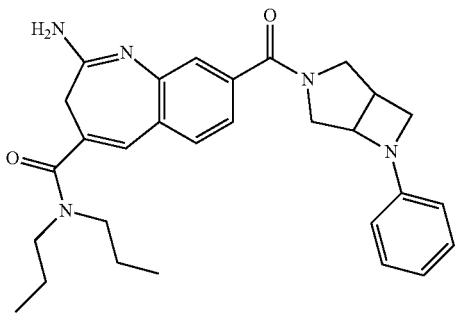 [SMILES: CCCN(CCC)C(=O)C1=Cc2ccc(C(=O)N3CC4CN(c5ccccc5)C4C3)cc2N=C(N)C1]

The title compound was prepared in analogy to Example 1 by using 6-phenyl-3, 6-diazabicyclo [3.2.0]heptane (compound 16A) instead of 2-(p-tolyl)-2,6-diazaspiro[3.3]heptane. Example 16 was obtained as a white solid (12 mg). $^1$H NMR (400 MHz, DMSO-d$_6$) δ ppm=7.55 (d, J=7.15 Hz, 1H), 7.41 (br. s., 2H), 7.14 (t, J=7.72 Hz, 2H), 6.96 (s, 1H), 6.65 (t, J=7.28 Hz, 1H), 6.40 (d, J=7.78 Hz, 2H), 4.64 (dd, J=4.08, 6.34 Hz, 1H), 3.88 (t, J=7.59 Hz, 1H), 3.58 (dd, J 3.45, 7.59 Hz, 1H), 3.51 (br. s., 1H), 3.28-3.44 (m, 10H), 1.61 (sxt, J=7.38 Hz, 4H), 0.88 (t, J=7.40 Hz, 6H). MS: calc'd 486 (M+H)$^+$, measured 486 (M+H)$^+$.

Preparation of Compound 16A: The title compound was prepared in analogy to compound 4B of Example 4 by using tert-butyl 3,6-diazabicyclo[3.2.0]heptane-3-carboxylate instead of tert-butyl 3-(aminomethyl)azetidine-1-carboxylate.

Example 17

2-Amino-8-[3-(benzylamino)azetidine-1-carbonyl]-N,N-dipropyl-3H-1-benzazepine-4-carboxamide

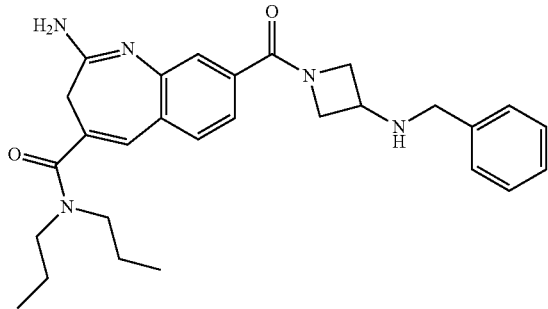 [SMILES: CCCN(CCC)C(=O)C1=Cc2ccc(C(=O)N3CC(NCc4ccccc4)C3)cc2N=C(N)C1]

The title compound was prepared in analogy to Example 1 by using tert-butyl azetidin-3-yl(benzyl)carbamate (compound 17A) instead of 2-(p-tolyl)-2,6-diazaspiro[3.3]heptane. Example 17 was obtained as a white solid (35 mg). $^1$H NMR (400 MHz, DMSO-d$_6$) δ ppm=7.71-7.51 (m, 8H), 7.09 (s, 1H), 4.75 (m, 1H), 4.52 (m, 2H), 4.32-4.27 (m, 4H), 3.47 (m, 4H), 3.37 (s, 2H), 1.75-1.66 (m, 4H), 0.98-0.93 (m, 6H). MS: calc'd 474 (M+H)$^+$, measured 474 (M+H)$^+$.

Preparation of Compound 17A:

The title compound was prepared in analogy to compound 3D of Example 3 by using phenylmethanamine instead of aniline.

Example 18

2-Amino-8-[3-[4-(aminomethyl)anilino]pyrrolidine-1-carbonyl]-N,N-dipropyl-3H-1-benzazepine-4-carboxamide

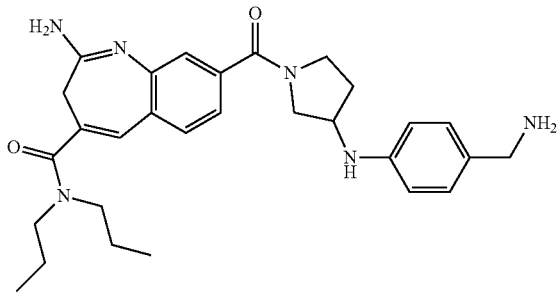 [SMILES: CCCN(CCC)C(=O)C1=Cc2ccc(C(=O)N3CCC(Nc4ccc(CN)cc4)C3)cc2N=C(N)C1]

The title compound was prepared in analogy to Example 1 by using tert-butyl azetidin-3-yl(benzyl)carbamate (compound 18G) instead of 2-(p-tolyl)-2,6-diazaspiro[3.3]heptane. Example 18 was obtained as a white solid (30 mg). $^1$H NMR (400 MHz, METHANOL-d$_4$) δ ppm=7.67-7.56 (m, 3H), 7.16-7.05 (m, 2H), 6.78-6.68 (m, 3H), 4.14-4.04 (m, 4H), 3.97-3.46 (m, 3H), 3.44-3.32 (m, 6H), 3.36-2.29 (m, 1H), 2.05-2.03 (m, 1H), 1.74-1.67 (m, 4H), 0.98-0.94 (m, 6H). MS: calc'd 503.3 (M+H)$^+$, measured 503.3 (M+H)$^+$.

Preparation of Compound 18G:

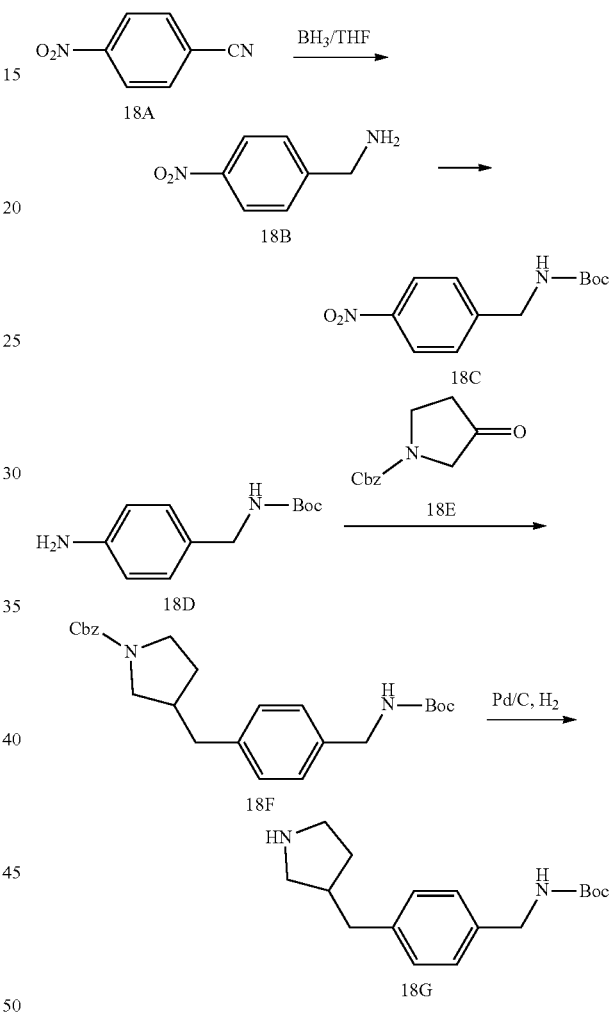

Step I: To a solution of 4-nitrobenzonitrile (compound 18A, 500 mg, 3.35 mmol) in THF (20 mL) was added BH$_3$/THF (1 M, 13.5 mL, 13.50 mmol) at 25° C. After the reaction mixture was stirred at 75° C. for 2 hrs, it was quenched by MeOH (10 mL). The solution was diluted with H$_2$O (100 mL) and extracted with EA (50 mL×3). The combined organic layers were washed with brine (30 mL×2), dried over Na$_2$SO$_4$ and concentrated to give (4-nitrophenyl)methanamine (compound 18B, 300 mg) as a yellow oil, which was used in the next step directly. MS: calc'd 153.1 (M+H)$^+$, measured 153.1 (M+H)$^+$.

Step II: To a solution of (4-nitrophenyl)methanamine (compound 18B, 300 mg, 1.97 mmol) and DIPEA (762 mg, 5.91 mmol) in DCM (20 mL) was added Boc$_2$O (472 mg, 2.17 mmol) at 0° C. Then the mixture was stirred at 25° C. for 1 hr. The reaction was quenched by saturated NH$_4$Cl (20 mL), diluted with H₂O (100 mL) and extracted with DCM (30 mL×3). The combined organic layers were washed with brine (20 mL×2), dried over Na₂SO₄ and concentrated. The crude product was purified by silica gel column chromatography (PE:EA=4:1) to give the tert-butyl 4-nitrobenzylcarbamate (compound 18C, 400 mg, 80.5%) as a colorless oil. MS: calc'd 253 (M+H)⁺, measured 253 (M+H)⁺.

Step III: To a solution of tert-butyl 4-nitrobenzylcarbamate (compound 18C, 400 mg, 1.59 mmol) and Pd/C (50 mg) in MeOH (15 mL) was stirred at 25° C. under H₂ atmosphere for 0.5 hr. The reaction mixture was filtered and the filtrate was concentrated to give tert-butyl 4-aminobenzylcarbamate (compound 18D, 300 mg) as a red solid, which was used in the next step directly. MS: calc'd 223 (M+H)⁺, measured 223 (M+H)⁺.

Step IV: To a solution of tert-butyl 4-aminobenzylcarbamate (compound 18D, 200 mg, 0.9 mmol) and benzyl 3-oxopyrrolidine-1-carboxylate (197 mg, 0.9 mmol) in DCM (10 mL) was added AcOH (65 mg, 1.08 mmol) and NaBH(OAc)₃ (267 mg, 1.26 mmol) at 0° C. After the reaction was heated at 40° C. for 18 hrs, it was quenched with NaOH (2 N, 20 mL), diluted with H₂O (100 mL) and extracted with DCM (20 mL×3). The combined organic layers were washed with brine (20 mL×2), dried over Na₂SO₄ and concentrated. The crude product was purified by silica gel chromatography (PE/EA=2:1) to give benzyl 3-((4-(((tert-butoxycarbonyl)amino)methyl)phenyl)amino)pyrrolidine-1-carboxylate (compound 18F, 300 mg, 78%) as a yellow solid. MS: calc'd 426 (M+H)⁺, measured 426 (M+H)⁺.

Step V: A suspension of benzyl 3-((4-(((tert-butoxycarbonyl) amino)methyl)phenyl) amino) pyrrolidine-1-carboxylate (compound 18F, 300 mg, 0.7 mmol) and Pd/C (50 mg) in MeOH (10 mL) was stirred at 25° C. under H₂ atmosphere for 1 hr. The reaction mixture was filtered and the filtrate was concentrated to give the crude product tert-butyl 4-(pyrrolidin-3-ylamino)benzylcarbamate (compound 18G, 200 mg) as a colorless oil, which was used in the next step directly. MS: calc'd 292 (M+H)⁺, measured 292 (M+H)⁺.

Example 19

2-Amino-8-[3-(benzylamino)pyrrolidine-1-carbonyl]-N,N-dipropyl-3H-1-benzazepine-4-carboxamide

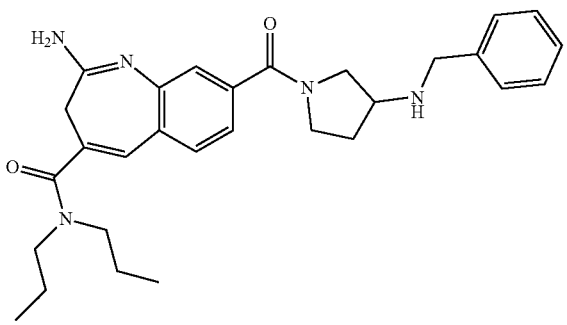 [SMILES: CCCN(CCC)C(=O)C1=Cc2ccc(C(=O)N3CCC(NCc4ccccc4)C3)cc2N=C(N)C1]

The title compound was prepared in analogy to Example 1 by using tert-butyl N-benzyl-N-pyrrolidin-3-yl-carbamate (Compound 19C) instead of 2-(p-tolyl)-2,6-diazaspiro[3.3]heptane. Example 19 was obtained as a white solid (40 mg). ¹H NMR (400 MHz, METHANOL-d₄) δ ppm=7.66 (d, J=8 Hz, 1H), 7.59-7.46 (m, 7H), 7.03 (s, 1H), 4.34-4.24 (m, 2H), 4.11-3.98 (m, 2H), 3.81-3.69 (m, 3H), 3.49-3.46 (m, 4H), 3.32 (s, 2H), 2.51-2.50 (br, 1H), 2.24-2.19 (br, 1H), 1.74-1.65 (m, 4H), 0.95 (br, 6H). MS: calc'd 488 (M+H)⁺, measured 488 (M+H)⁺.

Preparation of Compound 19C:

The title compound was prepared in analogy to compound 3D of Example 3 by using tert-butyl 3-oxopyrrolidine-1-carboxylate and phenylmethanamine instead of tert-butyl 3-oxoazetidine-1-carboxylate and aniline.

Example 20

2-amino-8-[4-(anilinomethyl)piperidine-1-carbonyl]-N,N-dipropyl-3H-1-benzazepine-4-carboxamide

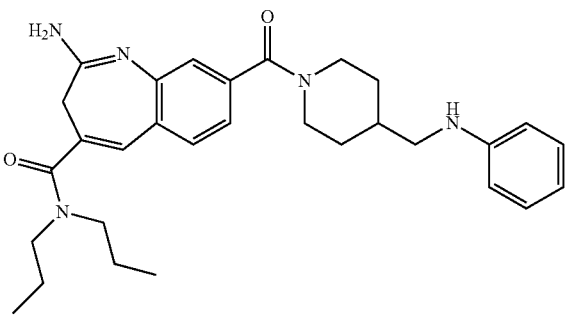 [SMILES: CCCN(CCC)C(=O)C1=Cc2ccc(C(=O)N3CCC(CNc4ccccc4)CC3)cc2N=C(N)C1]

The title compound was prepared in analogy to Example 1 by using N-(piperidin-4-ylmethyl)aniline (compound 20A) instead of 2-(p-tolyl)-2,6-diazaspiro[3.3]heptane. Example 20 was obtained as a white solid (18 mg). ¹H NMR (400 MHz, METHANOL-d₄) δ ppm=7.67-7.63 (d, J 8.40 Hz, 1H), 7.52-7.42 (m, 4H), 7.35-7.21 (m, 3H), 7.08 (s, 1H), 4.74-4.62 (d, J=10.40 Hz, 1H), 3.84-3.73 (d, J=10.40 Hz, 1H), 3.47 (br. s., 4H), 3.37 (s, 2H), 3.32-3.27 (m, 2H), 3.26-3.14 (m, 1H), 2.99-2.86 (m, 1H), 2.16-1.94 (m, 2H), 1.9-1.77 (m, 1H), 1.77-1.62 (m, 4H), 1.50-1.32 (m, 2H), 1.07-0.82 (m, 6H). MS: calc'd 502 (M+H)⁺, measured 502 (M+H)⁺.

Preparation of Compound 20A:

The title compound was prepared in analogy to compound 3D of Example 3 by using tert-butyl 4-formylpiperidine-1-carboxylate instead of tert-butyl 3-oxoazetidine-1-carboxylate.

Example 21

2-Amino-8-[3-(anilinomethyl)pyrrolidine-1-carbonyl]-N,N-dipropyl-3H-1-benzazepine-4-carboxamide

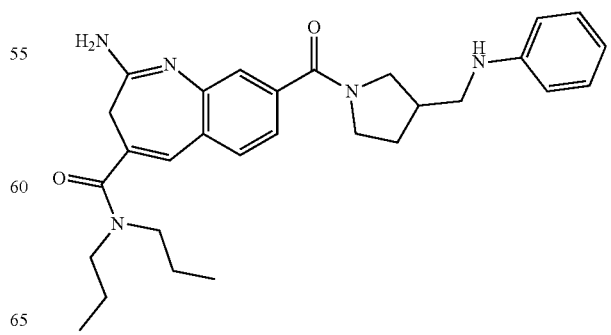

The title compound was prepared in analogy to Example 1 by using N-(piperidin-4-ylmethyl)aniline (compound 21A) instead of 2-(p-tolyl)-2,6-diazaspiro[3.3]heptane. Example 21 was obtained as a yellow solid (20 mg). $^1$H NMR (400 MHz, METHANOL-$d_4$) δ ppm=7.61-7.50 (m, 3H), 7.29-7.27 (m, 1H), 7.17-7.15 (m, 1H), 7.05 (s, 1H), 6.97-6.78 (m, 3H), 3.86-3.78 (m, 1H), 3.61-3.59 (m, 2H), 3.45 (br, 4H), 3.43-3.34 (m, 4H), 3.30-3.21 (m, 1H), 2.68-2.58 (m, 1H), 2.25-2.10 (m, 1H), 1.84-1.79 (m, 1H), 1.73-1.64 (m, 4H), 0.93 (br. s., 6H). MS: calc'd 488 (M+H)$^+$, measured 488 (M+H)$^+$.

Preparation of Compound 21A

The title compound was prepared in analogy to compound 3D of Example 3 by using tert-butyl 3-formylpyrrolidine-1-carboxylate instead of tert-butyl 3-oxoazetidine-1-carboxylate.

Example 22

2-Amino-8-[3-[(E)-but-2-enoxy]azetidine-1-carbonyl]-N,N-dipropyl-3H-1-benzazepine-4-carboxamide

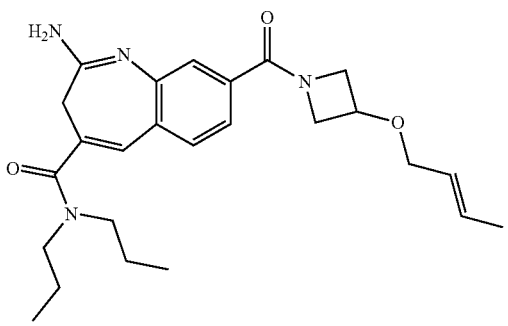 [SMILES: C/C=C/COC1CN(C(=O)c2ccc3c(c2)N=C(N)CC(C(=O)N(CCC)CCC)=C3)C1]

The title compound was prepared in analogy to Example 1 by using 3-[(E)-but-2-enoxy]azetidine (Compound 22B) instead of 2-(p-tolyl)-2,6-diazaspiro[3.3]heptane. Example 22 was obtained as a white solid (34.5 mg). $^1$H NMR (400 MHz, METHANOL-$d_4$) δ ppm=7.65-7.64 (m, 3H), 7.07 (s, 1H), 5.80-5.73 (m, 1H), 5.61-5.54 (m, 1H), 4.56-4.52 (m, 1H), 4.45-4.35 (m, 2H), 4.26-4.23 (m, 1H), 4.09-4.01 (m, 1H), 3.94-3.93 (m, 2H), 3.45 (br, 4H), 3.35 (s, 2H), 1.74-1.64 (m, 7H), 0.94 (br, 6H). MS: calc'd 439 (M+H)$^+$, measured 439 (M+H)$^+$.

Preparation of Compound 22B:

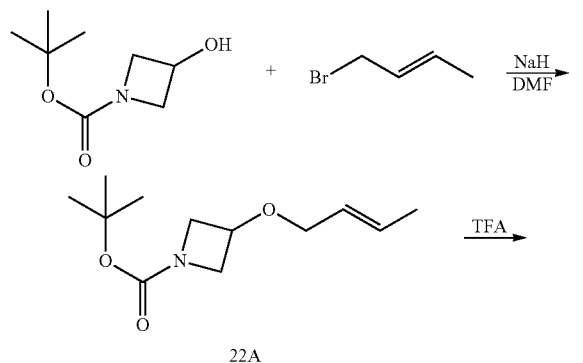

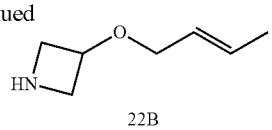

To a 25 mL flask was added tert-butyl 3-hydroxyazetidine-1-carboxylate (200 mg, 1.15 mmol) and DMF (4 mL). The solution was cooled with ice bath and NaH (69 mg, 1.73 mmol) was added portion-wise. The suspension was warmed to rt for 10 mins, and then it was cooled again. (E)-1-Bromobut-2-ene (156 mg, 119 µL, 1.15 mmol) was added. The final mixture was warmed to rt and stirred for 3 hrs. The reaction mixture was quenched with sat. NH$_4$Cl, diluted with 25 mL of water and extracted with EA (25 mL×2). The organic layer was washed with sat. NH$_4$Cl (25 mL×2), brine (25 mL), dried over Na$_2$SO$_4$ and concentrated to give 200 mg of yellow oil. Then it was purified by silica gel column chromatography (eluted with EA/PE=10-30%) to give 83 mg tert-butyl 3-[(E)-but-2-enoxy]azetidine-1-carboxylate (Compound 22A) as a colorless oil. MS: calc'd 228 (M+H)$^+$, measured 228 (M+H)$^+$.

Compound 22A was dissolved in DCM (4 mL) and TFA (0.5 mL) was added. The mixture was stirred at rt for 14 hrs. The solvent was removed in vacuo to give 3-[(E)-but-2-enoxy]azetidine (Compound 22B) as a colorless oil. MS: calc'd 128 (M+H)$^+$, measured 128 (M+H)$^+$.

Example 23

2-Amino-8-(3-anilinopiperidine-1-carbonyl)-N,N-dipropyl-3H-1-benzazepine-4-carboxamide

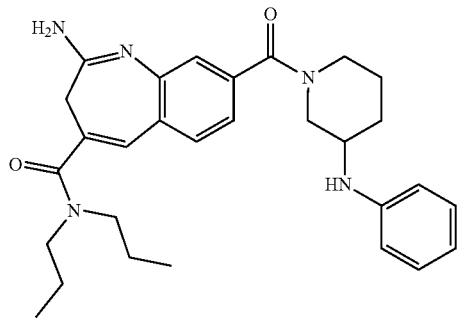 [SMILES: CCCN(CCC)C(=O)C1=Cc2ccc(C(=O)N3CCCC(Nc4ccccc4)C3)cc2N=C(N)C1]

The title compound was prepared in analogy to Example 1 by using N-phenylpiperidin-3-amine (Compound 23B) instead of 2-(p-tolyl)-2,6-diazaspiro[3.3]heptane. Example 23 was obtained as a white solid (40 mg). $^1$H NMR (400 MHz, METHANOL-$d_4$) δ ppm=7.64-7.46 (m, 2H), 7.33-7.18 (m, 2H), 7.07-6.91 (m, 3H), 6.53-6.44 (m, 2H), 4.75-4.65 (br, 1H), 3.88 (br, 1H), 3.66-3.64 (m, 1H), 3.53-3.44 (m, 6H), 3.31 (s, 2H), 2.15-2.06 (m, 2H), 1.80-1.64 (m, 6H), 0.94 (br, 6H). MS: calc'd 488 (M+H)$^+$, measured 488 (M+H)$^+$.

Preparation of Compound 23B:

The title compound was prepared in analogy to compound 3D of Example 3 by using tert-butyl 3-oxopiperidine-1-carboxylate instead of tert-butyl 3-oxoazetidine-1-carboxylate.

Example 24

2-Amino-8-[3-(benzylamino)piperidine-1-carbonyl]-N,N-dipropyl-3H-1-benzazepine-4-carboxamide

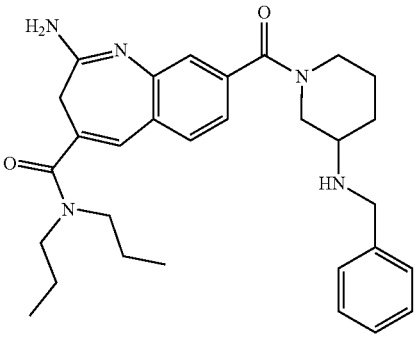 [SMILES: CCCN(CCC)C(=O)C1=Cc2ccc(C(=O)N3CCCC(NCc4ccccc4)C3)cc2N=C(N)C1]

The title compound was prepared in analogy to Example 1 by using tert-butyl N-benzyl-N-(3-piperidyl)carbamate (Compound 24B) instead of 2-(p-tolyl)-2,6-diazaspiro[3.3]heptane. Example 24 was obtained as a white solid (49 mg). $^1$H NMR (400 MHz, METHANOL-$d_4$) δ ppm=7.65 (d, J=8 Hz, 1H), 7.54-7.48 (m, 7H), 7.07 (s, 1H), 4.75-4.72 (br, 1H), 4.37 (br, 2H), 3.69-3.68 (br, 1H), 3.46 (m, 5H), 3.36 (s, 2H), 3.31-3.30 (m, 2H), 2.38 (br, 1H), 1.86-1.65 (m, 7H), 0.94 (br, 6H). MS: calc'd 502 (M+H)$^+$, measured 502 (M+H)$^+$.

Preparation of Compound 24B:

The title compound was prepared in analogy to compound 3D of Example 3 by using tert-butyl 3-oxopiperidine-1-carboxylate and phenylmethanamine instead of tert-butyl 3-oxoazetidine-1-carboxylate and aniline.

Example 25

2-Amino-8-(3-butoxyazetidine-1-carbonyl)-N,N-dipropyl-3H-1-benzazepine-4-carboxamide

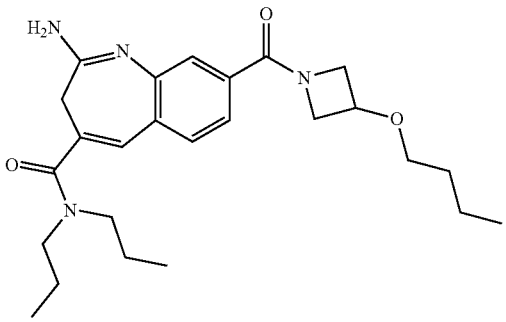 [SMILES: CCCCOC1CN(C(=O)c2ccc3c(c2)N=C(N)CC(C(=O)N(CCC)CCC)=C3)C1]

The title compound was prepared in analogy to Example 1 by using 3-butoxyazetidine (Compound 25B) instead of 2-(p-tolyl)-2,6-diazaspiro[3.3]heptane. Example 25 was obtained as a white solid (29 mg). $^1$H NMR (400 MHz, METHANOL-$d_4$) δ ppm=7.67-7.62 (m, 3H), 7.07 (s, 1H), 4.58-4.54 (m, 1H), 4.42-4.37 (m, 2H), 4.26-4.23 (m, 1H), 4.04-3.99 (m, 1H), 3.47-3.42 (m, 6H), 3.35 (s, 2H), 1.74-1.65 (m, 4H), 1.61-1.54 (m, 2H), 1.46-1.36 (m, 2H), 0.96-0.92 (m, 9H). MS: calc'd 441 (M+H)$^+$, measured 441 (M+H)$^+$.

Preparation of Compound 25B:

The title compound was prepared in analogy to compound 22B of Example 22 by using 1-bromobutane instead of (E)-1-bromobut-2-ene.

The invention claimed is:

1. A benzazepine-4-carboxamide compound of the formula

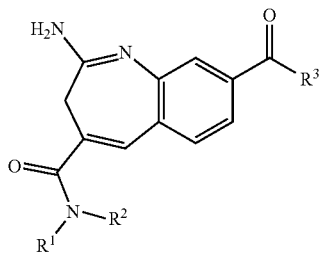

I wherein $R^1$ is $C_{3-7}$-alkyl;
$R^2$ is $C_{3-7}$-alkyl or $C_{3-7}$-cycloalkyl-$C_{1-7}$-alkyl;
$R^3$ is a heterocycle selected from

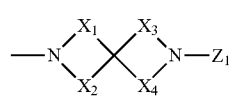

a)

wherein $X_1$ is $(CH_2)_m$ wherein m is 1 or 2;
$X_2$ is $(CH_2)_n$ wherein n is 1 or 2;
$X_3$ is $(CH_2)_o$ wherein o is 1 or 2;
$X_4$ is $(CH_2)_p$ wherein p is 1 or 2; and
$Z_1$ is phenyl, wherein phenyl is unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl and di-$C_{1-7}$-alkyl-amino-$C_{1-7}$-alkyl; or

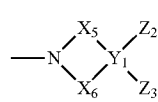

b)

wherein $X_5$ is $(CH_2)_q$ wherein q is 1 or 2;
$X_6$ is $(CH_2)_r$ wherein r is 1 or 2;
$Y_1$ is a carbon or nitrogen atom and
$Z_2$ is hydrogen and
$Z_3$ is selected from the group consisting of hydrogen, $C_{1-7}$-alkoxy, $C_{2-7}$-alkenyloxy, phenyl, phenyl-$C_{1-7}$-alkyl, phenyl-$C_{1-7}$-alkyloxy, phenyl-$C_{1-7}$-alkylamino, phenylamino-$C_{1-7}$-alkyl, phenylamino, wherein phenyl is unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl and di-$C_{1-7}$-alkyl-amino-$C_{1-7}$-alkyl;

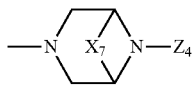

c)

wherein

X₇ is (CH₂)ₛ wherein s is 1 or 2; and

Z₄ is phenyl, wherein phenyl is unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl and di-$C_{1-7}$-alkyl-amino-$C_{1-7}$-alkyl; or

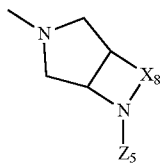

d)

wherein

X₈ is (CH₂)ₜ wherein t is 1 or 2; and

Z₅ is phenyl, wherein phenyl is unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl and di-$C_{1-7}$-alkyl-amino-$C_{1-7}$-alkyl, or a pharmaceutically acceptable salt thereof.

2. The compound of claim 1, wherein $R^1$ and $R^2$ are n-propyl.

3. The compound of claim 1, wherein $R^3$ has the formula a)

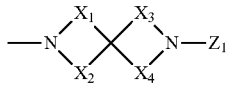

a)

wherein

X₁ is (CH₂)ₘ wherein m is 1 or 2;

X₂ is (CH₂)ₙ wherein n is 1 or 2;

X₃ is (CH₂)ₒ wherein o is 1 or 2;

X₄ is (CH₂)ₚ wherein p is 1 or 2; and

Z₁ is phenyl, wherein phenyl is unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl and di-$C_{1-7}$-alkyl-amino-$C_{1-7}$-alkyl.

4. The compound of claim 3, wherein $Z_1$ is phenyl or $C_{1-7}$-alkylphenyl.

5. The compound of claim 3, wherein m is 1 and n is 1.

6. The compound of claim 3, wherein o is 1 and p is 1 or wherein o is 2 and p is 2.

7. The compound of claim 1, wherein m is 2, n is 2, o is 1 and p is 1.

8. The compound of claim 1, wherein $R^3$ has the formula b)

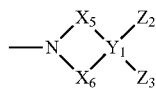

b)

wherein

X₅ is (CH₂)_q wherein q is 1 or 2;

X₆ is (CH₂)_r wherein r is 1 or 2;

Y₁ is a carbon or nitrogen atom and

Z₂ is hydrogen and

Z₃ is selected from the group consisting of hydrogen, $C_{1-7}$-alkoxy, $C_{2-7}$-alkenyloxy, phenyl, phenyl-$C_{1-7}$-alkyl, phenyl-$C_{1-7}$-alkyloxy, phenyl-$C_{1-7}$-alkylamino, phenylamino-$C_{1-7}$-alkyl, phenylamino, wherein phenyl is unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl and di-$C_{1-7}$-alkyl-amino-$C_{1-7}$-alkyl.

9. The compound of claim 8, wherein $Y_1$ is C.

10. The compound of claim 8, wherein $Y_1$ is N.

11. The compound of claim 8, wherein $Z_3$ is selected from the group consisting of phenyl, phenyl-$C_{1-7}$-alkyl, phenyl-$C_{1-7}$-alkyloxy, phenyl-$C_{1-7}$-alkylamino, phenylamino-$C_{1-7}$-alkyl, phenylamino and amino-$C_{1-7}$-alkylphenyl.

12. The compound of claim 8, wherein $Z_3$ is $C_{1-7}$-alkoxy or $C_{2-7}$-alkenyloxy.

13. The compound of claim 8, wherein q is 1 and r is 1.

14. The compound of claim 8, wherein q is 2 and r is 2.

15. The compound of claim 8, wherein q is 2 and r is 1.

16. The compound of claim 1, wherein $R^3$ has the formula c)

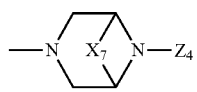

c)

wherein

X₇ is (CH₂)ₛ wherein s is 1 or 2; and

Z₄ is phenyl, wherein phenyl is unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl and di-$C_{1-7}$-alkyl-amino-$C_{1-7}$-alkyl.

17. The compound of claim 1, wherein $R^3$ has the formula d)

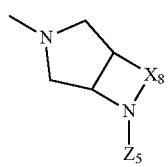

d)

wherein

X₈ is (CH₂)ₜ wherein t is 1 or 2; and $Z_5$ is phenyl, wherein phenyl is unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl and di-$C_{1-7}$-alkyl-amino-$C_{1-7}$-alkyl.

18. The compound of formula I according to claim 1, selected from:

2-amino-N,N-dipropyl-8-[6-(p-tolyl)-2,6-diazaspiro[3.3]heptane-2-carbonyl]-3H-1-benzazepine-4-carboxamide;

2-amino-8-(4-anilinopiperidine-1-carbonyl)-N,N-dipropyl-3H-1-benzazepine-4-carboxamide;

2-amino-8-(3-anilinoazetidine-1-carbonyl)-N,N-dipropyl-3H-1-benzazepine-4-carboxamide;

2-amino-8-[3-(anilinomethyl)azetidine-1-carbonyl]-N,N-dipropyl-3H-1-benzazepine-4-carboxamide;

2-amino-8-(3-anilinopyrrolidine-1-carbonyl)-N,N-dipropyl-3H-1-benzazepine-4-carboxamide;

2-amino-8-(4-phenylpiperazine-1-carbonyl)-N,N-dipropyl-3H-1-benzazepine-4-carboxamide;

2-amino-8-(7-phenyl-2,7-diazaspiro[3.4]octane-2-carbonyl)-N,N-dipropyl-3H-1-benzazepine-4-carboxamide;

2-amino-N,N-dipropyl-8-(pyrrolidine-1-carbonyl)-3H-1-benzazepine-4-carboxamide;

2-amino-8-(4-anilinopiperidine-1-carbonyl)-N-(cyclopropylmethyl)-N-propyl-3H-1-benzazepine-4-carboxamide;

2-amino-8-(4-benzylpiperazine-1-carbonyl)-N,N-dipropyl-3H-1-benzazepine-4-carboxamide;

2-amino-8-(3-benzyloxyazetidine-1-carbonyl)-N,N-dipropyl-3H-1-benzazepine-4-carboxamide;

2-amino-8-(6-phenyl-3,6-diazabicyclo[3.1.1]heptane-3-carbonyl)-N,N-dipropyl-3H-1-benzazepine-4-carboxamide;

2-amino-8-(2-phenyl-2,7-diazaspiro[3.5]nonane-7-carbonyl)-N,N-dipropyl-3H-1-benzazepine-4-carboxamide;

2-amino-8-(7-phenyl-2,7-diazaspiro[3.5]nonane-2-carbonyl)-N,N-dipropyl-3H-1-benzazepine-4-carboxamide;

2-amino-8-(8-phenyl-3,8-diazabicyclo[3.2.1]octane-3-carbonyl)-N,N-dipropyl-3H-1-benzazepine-4-carboxamide;

2-amino-8-(6-phenyl-3,6-diazabicyclo[3.2.0]heptane-3-carbonyl)-N,N-dipropyl-3H-1-benzazepine-4-carboxamide;

2-amino-8-[3-(benzylamino)azetidine-1-carbonyl]-N,N-dipropyl-3H-1-benzazepine-4-carboxamide, 2-amino-8-[3-[4-(aminomethyl)anilino]pyrrolidine-1-carbonyl]-N,N-dipropyl-3H-1-benzazepine-4-carboxamide;

2-amino-8-[3-(benzylamino)pyrrolidine-1-carbonyl]-N,N-dipropyl-3H-1-benzazepine-4-carboxamide;

2-amino-8-[4-(anilinomethyl)piperidine-1-carbonyl]-N,N-dipropyl-3H-1-benzazepine-4-carboxamide;

2-amino-8-[3-(anilinomethyl)pyrrolidine-1-carbonyl]-N,N-dipropyl-3H-1-benzazepine-4-carboxamide;

2-amino-8-[3-[(E)-but-2-enoxy]azetidine-1-carbonyl]-N,N-dipropyl-3H-1-benzazepine-4-carboxamide;

2-amino-8-(3-anilinopiperidine-1-carbonyl)-N,N-dipropyl-3H-1-benzazepine-4-carboxamide, 2-amino-8-[3-(benzylamino)piperidine-1-carbonyl]-N,N-dipropyl-3H-1-benzazepine-4-carboxamide; or 2-amino-8-(3-butoxyazetidine-1-carbonyl)-N,N-dipropyl-3H-1-benzazepine-4-carboxamide, or a pharmaceutically acceptable salt thereof.

19. A pharmaceutical composition comprising a compound of formula I according to claim 1, or a pharmaceutically acceptable salt thereof, and a pharmaceutically acceptable carrier and/or adjuvant.

20. A method of treating cancer, autoimmune diseases, inflammation, sepsis, allergy, asthma, graft rejection, graft-versus-host disease, immunodeficiencies, or infectious diseases, the method comprising administering to a subject a therapeutically effective amount of a compound of formula I as defined in claim 1, or a pharmaceutically acceptable salt thereof.

21. A process for the manufacture of a compound of formula I as defined in claim 1, which process comprises:

a) coupling a compound of the formula II

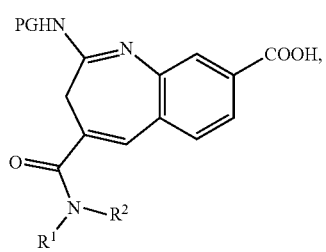

wherein $R^1$ and $R^2$ are as defined in claim 1 and PG is a protecting group, with an amine of the formula III $R^3H$      III wherein $R^3$ is defined herein before, under basic conditions in the presence of a coupling agent and removing the protecting group PG under acidic conditions to obtain a compound of the formula I

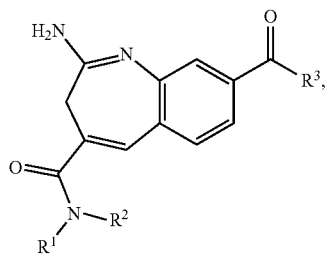

wherein $R^1$ to $R^3$ are as defined in claim 1, and, if desired, converting the compound obtained into a pharmaceutically acceptable salt.

* * * * *